United States Patent [19]
Gallie et al.

[11] Patent Number: 6,063,567
[45] Date of Patent: *May 16, 2000

[54] METHOD, REAGENTS AND KIT FOR DIAGNOSIS AND TARGETED SCREENING FOR RETINOBLASTOMA

[75] Inventors: Brenda L. Gallie, Toronto; James M. Dunn, Scarborough; John K. Stevens; May Hui, both of Toronto, all of Canada

[73] Assignee: Visible Genetics Inc., Toronto, Canada

[ * ] Notice: This patent is subject to a terminal disclaimer.

[21] Appl. No.: 08/779,916

[22] Filed: Jan. 7, 1997

Related U.S. Application Data

[63] Continuation of application No. PCT/US95/08604, Jul. 7, 1995, which is a continuation of application No. 08/271,942, Jul. 8, 1994, Pat. No. 5,550,020.

[51] Int. Cl.⁷ ............................. C12Q 1/68; C07H 21/04; C12P 19/34
[52] U.S. Cl. ........................... 435/6; 435/91.2; 536/23.5; 536/24.31; 536/24.33
[58] Field of Search .................................. 435/6, 4, 91.1, 435/91.2; 536/23.1, 24.31, 24.33, 23.5

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,942,123 | 7/1990 | Lee et al. | 435/6 |
| 5,011,773 | 4/1991 | Lee et al. | 435/69.1 |
| 5,266,459 | 11/1993 | Beutler et al. | 435/6 |
| 5,550,020 | 8/1996 | Gaillie et al. | 435/6 |
| 5,582,989 | 12/1996 | Caskey et al. | 435/6 |

FOREIGN PATENT DOCUMENTS

| | | |
|---|---|---|
| 0259031 | 9/1988 | European Pat. Off. . |
| 0390530 | 3/1990 | European Pat. Off. . |
| 0539970 | 5/1993 | European Pat. Off. . |
| 0608004 | 7/1994 | European Pat. Off. . |
| 89/06703 | 7/1989 | WIPO . |
| 90/12807 | 1/1990 | WIPO . |
| 91/10734 | 1/1991 | WIPO . |
| 92/01066 | 1/1992 | WIPO . |
| 93/15227 | 5/1993 | WIPO . |
| 93/18177 | 9/1993 | WIPO . |
| 93/23539 | 11/1993 | WIPO . |
| 94/01467 | 1/1994 | WIPO . |

OTHER PUBLICATIONS

Breslauer et al., "Predicting DNA Duplex Stability from base sequence", *Proc. Nat'l Acad. Sci. USA* 83: 3746=3750 (1986).

Canning et al., "Short direct repeats at the breakpoints of deletions of the retinoblastoma gene", *Proc. Nat'l Acad. Sci. USA* 86: 5044–5048 (1989).

(List continued on next page.)

*Primary Examiner*—Carla J. Myers
*Attorney, Agent, or Firm*—Oppendahl & Larson LLP

[57] ABSTRACT

Reliable and cost effective testing for mutations in the RB1 gene can be accomplished by (a) quantitatively amplifying exons of the sample RB1 gene using primers complementary to intron regions flanking each exon; and (b) determining the lengths and/or quantities of the amplification products for each exon and comparing that length or quantity to the length or quantity of amplification products obtained when a wild-type RB1 gene is amplified using the same primers. Differences in length between an amplified sample exon and the corresponding amplified wild-type exon reflect the occurrence on an insertion or deletion mutation in the sample RB1 gene. Differences in quantity reflect the complete absence of an exon, or heterozygosity for a mutant exon. Next, the nucleic acid sequence of each exon found to contain an insertion or deletion mutation is determined, or of all exons in the event no insertion or deletion mutations are identified. Preferably, the amplification of the exons is multiplexed so that more than one exon is amplified in a single vessel using sets of primers which provide gene fragments of distinctive lengths when used to amplify a normal RB1 gene.

27 Claims, 3 Drawing Sheets

OTHER PUBLICATIONS

DerKinderen et al., "Early Diagnosis of Bilateral Retinoblastoma Reduces Death and Blindness", *Int. J. Cancer* 44: 35–39 (1989).

Dryja, T.P., "DNA Testing for Retinoblastoma", *Arch. Ophthalmol.* 109: 1210 (1991).

Dryja et al., "Molecular etiology of low–penetrance retinoblastoma in two pedigrees", *Amer. J. Genetics* 52: 1122–1128 (1993).

Dunn et al., "Sequence based diagnosis of Retinoblastoma", Keystone Symposium on Tumor Supresor Genes, Taos, New Mexico, Feb. 13–20, 1994, *J. Cellular Biochem Supp*: 199 (1994).

Dunn, et al., "Mutations in the RB1 Gene and Their Effects on Transcription", *Molecular and Cellular Biology* 9: 4596–4604 (1989).

Dunn et al., "Identification of Germline and Somatic Mutations Affecting the Retinoblastoma Gene", *Science* 241: 1797–1800 (1988).

Friend et al., "A human DNA Segment with Properties of the Gene that Predisposes to Retinoblastoma and Osteosarcoma" *Nature* 323: 643–6 (1986).

Gallie, B.L. "The Misadventures of RB1" in *Causes and Consequences of Chromsomal Aberrations*, pp. 429–446, CRC Press (1993).

Goddard et al., "Use of the RB1 cDNA as a diagnostic prove in retinoblastoma families", *Clin. Genetics* 37: 117–26 (1990).

Horsthhemke et al., "Early diagnosis of hereditary retinoblastoma by detection of molecular deletions at gene locus", *Lancet* 1: 511–512 (1987).

Horsthemke et al., "Detection of submicroscopic deletions and a DNA polymorphism at the retinoblastoma locus" *Human Genetics* 76: 257–61 (1987).

Lee et al., "Diverse mutations lead to inactivation of the retinoblastoma gene", *Prog. Clin. Biol. Res.* 362: 221–240 (1991).

Lee et al., "Human retinoblastoma susceptibility gene: cloning, identification and sequence", *Science* 235: 1394–1399 (1987).

Lee et al. "The retinoblastoma susceptibility gene encodes a nuclear phosphoprotein associated with DNA binding activity", *Nature* 329: 642–645 (1987).

Lohmann et al., "Detection of small RB1 deletions in retinoblastoma by multiplex PCR and high resolution gel electrophoresis" *Human Genetics* 89: 49–53 (1992).

Orita, et al., "Detection of polymorphisms of human DNA by gel electrophoresis as single–strand conformation polymorphisms", *Proc. Nat'l. Acad. Sci. USA* 86:2766–2770 (1989).

Rychlik, W., "Selection of Primers for Polymerase Chain Reaction", *Methods in Molecular Biology, vol. 15: PCR Protocols: Current Methods and Applications*, pp. 31–40 (1993).

Sasano et al., "An analysis of abnormalities of the retinoblstoma gene in human ovarian and endometrial carcinoma", *Cancer* 66: 2150–2154 (1990).

Savard–McQuigge et al., *Your Child Has Retinoblastoma*, Canadian Cancer Society (1992).

Toguchida et al., "Complete genomic sequence of the human retinoblastoma susceptibility gene", *Genomics* 17L 535–543 (1993).

Wiggs, et al., "Prediction of the risk of hereditary retinoblastoma using DNA polymorphisms within the retinoblastoma gene", *N. Engl. J. Med.* 318: 151–157 (1988).

Yandell et al., "Oncogenic point mutations in the human retinoblastoma gene: their application to genetic counseling", *N. Engl. J. Med.* 321: 1689–1694 (1989).

Shimizu et al., "Detection of Mutations of the RB1 Gene in Retinoblastoma Patients by Using Exon–by–Exon PCR–SSCP Analysis" *Am. J. Hum. Genet.*. 54: 793–800 (1994).

Sachse et al., "DNA Aberrations at the Retinoblastoma Gene Locus in Human Squamous Cell Carcinomas of the Lung" *Oncogene* 9: 39–47 (1994).

McConkey, in *Human Genetics, The Molecular Revolution*, Jones & Bartlett, NY 1993, pp. 192–197.

Innis et al., *PCR Protocols: A Guide to Methods and Applications*, Academic Press, 1990 pp. 3–13, 7–76.

Yandell et al. The New England Journal of Medicine 321: 1689–1695, 1989.

Dryja et al. Am. J. of Hum. Gen 52: 1122–1128, 1993.

Dunn et al. Molecular and Cellular Biology 9: 4596–4604, 1989.

Lee et al. In Molecular Biology of hte Retina: Basic and Clinically Relevant Studies, pp 221–240, 1991.

Sachse et al. Oncogene 9: 39–47, 1994.

Shimizu et al. Am J. of Human Genetics 54: 793–800, 1994.

Beggs et al. Hum Gen. 86: 45–48, abstract only provided, 1990.

Falcaoconceicao et al. Revisto Brasileira de Genetica 15: 657–666, abstract only provided, 1992.

Rossiter et al. Genomics 9: 247–256, abstract only provided, 1991.

Toguchida et al. Genomics 17: 535–543, 1993.

Rychlik In Methods in Molecular Biology, vol. 15: PCR Protocols: Current Methods and Applications, Ed. B.A. White, Humana Press, Totawa, NJ Ch 2, 1993.

Lohmann et al. Human Genetics 89: 49–53, 1992.

SEQUENCE LISTING (1) GENERAL INFORMATION:

(iii) NUMBER OF SEQUENCES: 123

(2) INFORMATION FOR SEQ ID NO:1:

(i) SEQUENCE CHARACTERISTICS:
      (A) LENGTH: 22
      (B) TYPE: nucleic acid
      (C) STRANDEDNESS: single
      (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
      (A) ORGANISM: human (ix) FEATURE:

(A) NAME/KEY: primer for exon 2 of human RB1 gene (xi) SEQUENCE DESCRIPTION: SEQ ID NO:1:

ACTGTGTGGT ATCCTTATTT TG                                                22

(2) INFORMATION FOR SEQ ID NO:2:

(i) SEQUENCE CHARACTERISTICS:
          (A) LENGTH: 23
          (B) TYPE: nucleic acid
          (C) STRANDEDNESS: single
          (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
          (A) ORGANISM: human (ix) FEATURE:
          (A) NAME/KEY: primer for exon 2 of human RB1 gene (xi) SEQUENCE DESCRIPTION: SEQ ID NO:2:

ATAGTGATTT GAAGTTGGTT TTA                                               23

(2) INFORMATION FOR SEQ ID NO:3:

(i) SEQUENCE CHARACTERISTICS:
          (A) LENGTH: 23
          (B) TYPE: nucleic acid
          (C) STRANDEDNESS: single
          (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
          (A) ORGANISM: human (ix) FEATURE:
          (A) NAME/KEY: primer for exon 3 of human RB1 gene (xi) SEQUENCE DESCRIPTION: SEQ ID NO:3:

ATACAGTTTT AACATAGTAT CCA                                               23

(2) INFORMATION FOR SEQ ID NO:4:

(i) SEQUENCE CHARACTERISTICS:
          (A) LENGTH: 22
          (B) TYPE: nucleic acid
          (C) STRANDEDNESS: single
          (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
          (A) ORGANISM: human

```
    (ix) FEATURE:
        (A) NAME/KEY: primer for exon 3 of human RB1 gene (xi) SEQUENCE DESCRIPTION: SEQ ID NO:4:

AAGTCTATTG AGAGGAAAAT CC                                              22

(2) INFORMATION FOR SEQ ID NO:5:

(i) SEQUENCE CHARACTERISTICS:
        (A) LENGTH: 22
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 5 of human RB1 gene (xi) SEQUENCE DESCRIPTION: SEQ ID NO:5:

CTACTATGAC TTCTAAATTA CG                                              22

(2) INFORMATION FOR SEQ ID NO:6:

(i) SEQUENCE CHARACTERISTICS:
        (A) LENGTH: 22
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 5 of human RB1 gene (xi) SEQUENCE DESCRIPTION: SEQ ID NO:6:

TCAAGATGTT TGAGATTATT CC                                              22

(2) INFORMATION FOR SEQ ID NO:7:

(i) SEQUENCE CHARACTERISTICS:
        (A) LENGTH: 21
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal
```

(vi) ORIGINAL SOURCE:
             (A) ORGANISM: human (ix) FEATURE:
             (A) NAME/KEY: primer for exon 13 of human RB1 gene (xi) SEQUENCE DESCRIPTION: SEQ ID NO:7:

TGCTTATGTT CAGTAGTTGT G                                         21

(2) INFORMATION FOR SEQ ID NO:8:

(i) SEQUENCE CHARACTERISTICS:
             (A) LENGTH: 21
             (B) TYPE: nucleic acid
             (C) STRANDEDNESS: single
             (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
             (A) ORGANISM: human (ix) FEATURE:
             (A) NAME/KEY: primer for exon 13 of human RB1 gene (xi) SEQUENCE DESCRIPTION: SEQ ID NO:8:

TAATGGGGTG GGAGGTAGTT T                                         21

(2) INFORMATION FOR SEQ ID NO:9:

(i) SEQUENCE CHARACTERISTICS:
             (A) LENGTH: 22
             (B) TYPE: nucleic acid
             (C) STRANDEDNESS: single
             (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
             (A) ORGANISM: human (ix) FEATURE:
             (A) NAME/KEY: primer for exon 25 of human RB1 gene (xi) SEQUENCE DESCRIPTION: SEQ ID NO:9:

TCAAACTATA ACTTGAGGTT GC                                        22

(2) INFORMATION FOR SEQ ID NO:10:

(i) SEQUENCE CHARACTERISTICS:
             (A) LENGTH: 22
             (B) TYPE: nucleic acid
             (C) STRANDEDNESS: single
             (D) TOPOLOGY: linear (ii) MOLECULE TYPE: genomic DNA (iii) HYPOTHETICAL: no (iv) ANTI-SENSE: no

```
        (v) FRAGMENT TYPE: internal (vi) ORIGINAL SOURCE:
            (A) ORGANISM: human (ix) FEATURE:
            (A) NAME/KEY: primer for exon 25 of human RB1 gene (xi) SEQUENCE DESCRIPTION: SEQ ID NO:10:

AAAGAAATTG GTATAAGCCA GG                                              22

(2) INFORMATION FOR SEQ ID NO:11:

(i) SEQUENCE CHARACTERISTICS:
            (A) LENGTH: 19
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
            (A) ORGANISM: human (viii) POSITION IN GENOME:
            (A) CHROMOSOME/SEGMENT: chromosome 15

(ix) FEATURE:
            (A) NAME/KEY: primer amplification of control region of
                chromsome 15

(xi) SEQUENCE DESCRIPTION: SEQ ID NO:11:

CTCACCCGCA CCTAAGTTT                                                  19

(2) INFORMATION FOR SEQ ID NO:12:

(i) SEQUENCE CHARACTERISTICS:
            (A) LENGTH: 21
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
            (A) ORGANISM: human (viii) POSITION IN GENOME:
            (A) CHROMOSOME/SEGMENT: chromosome 15

(ix) FEATURE:
            (A) NAME/KEY: primer amplification of control region of
                chromsome 15

(xi) SEQUENCE DESCRIPTION: SEQ ID NO:12:

CCAGGATGAG AGCGGATGGC A                                               21

(2) INFORMATION FOR SEQ ID NO:13:

(i) SEQUENCE CHARACTERISTICS:
            (A) LENGTH: 19
```

```
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 1 of human RB1 gene (xi) SEQUENCE DESCRIPTION: SEQ ID NO:13:

GCCCCAGTTC CCCACAGAC                                                 19

(2) INFORMATION FOR SEQ ID NO:14:

(i) SEQUENCE CHARACTERISTICS:
        (A) LENGTH: 19
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 1 of human RB1 gene (xi) SEQUENCE DESCRIPTION: SEQ ID NO:14:

ACCCCTCGCC CAAGAACCC                                                 19

(2) INFORMATION FOR SEQ ID NO:15:

(i) SEQUENCE CHARACTERISTICS:
        (A) LENGTH: 21
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 8 of human RB1 gene (xi) SEQUENCE DESCRIPTION: SEQ ID NO:15:

TCTAATGAAA CCTAATAAGT A                                              21

(2) INFORMATION FOR SEQ ID NO:16:
```

(i) SEQUENCE CHARACTERISTICS:
            (A) LENGTH: 21
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
            (A) ORGANISM: human (ix) FEATURE:
            (A) NAME/KEY: primer for exon 8 of human RB1 gene (xi) SEQUENCE DESCRIPTION: SEQ ID NO:16:

TGCTCATAAC AAAAGAAGTA A                                              21

(2) INFORMATION FOR SEQ ID NO:17:

(i) SEQUENCE CHARACTERISTICS:
            (A) LENGTH: 21
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
            (A) ORGANISM: human (ix) FEATURE:
            (A) NAME/KEY: primer for exon 18 of human RB1 gene (xi) SEQUENCE DESCRIPTION: SEQ ID NO:17:

TTTTTGTGTG TGGGAAGTAC A                                              21

(2) INFORMATION FOR SEQ ID NO:18:

(i) SEQUENCE CHARACTERISTICS:
            (A) LENGTH: 22
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
            (A) ORGANISM: human (ix) FEATURE:
            (A) NAME/KEY: primer for exon 18 of human RB1 gene (xi) SEQUENCE DESCRIPTION: SEQ ID NO:18:

ATTCTATTCC CTACAGTTTC TT                                             22

(2) INFORMATION FOR SEQ ID NO:19:

(i) SEQUENCE CHARACTERISTICS:
        (A) LENGTH: 20
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 21 of human RB1 gene (xi) SEQUENCE DESCRIPTION: SEQ ID NO:19:

GGCTAAAAGA AGAAAAATGG        20

(2) INFORMATION FOR SEQ ID NO:20:

(i) SEQUENCE CHARACTERISTICS:
        (A) LENGTH: 20
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 21 of human RB1 gene (xi) SEQUENCE DESCRIPTION: SEQ ID NO:20:

TTACCTATGT TATGTTATGG        20

(2) INFORMATION FOR SEQ ID NO:21:

(i) SEQUENCE CHARACTERISTICS:
        (A) LENGTH: 22
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 22 of human RB1 gene (xi) SEQUENCE DESCRIPTION: SEQ ID NO:21:

TATGTGCTTC TTACCAGTCA AA        22

(2) INFORMATION FOR SEQ ID NO:22:

(i) SEQUENCE CHARACTERISTICS:
        (A) LENGTH: 22
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 23 of human RB1 gene (xi) SEQUENCE DESCRIPTION: SEQ ID NO:22:

GGAGTCATTT TTGTTGGTGT TG                                          22

(2) INFORMATION FOR SEQ ID NO:23:

(i) SEQUENCE CHARACTERISTICS:
        (A) LENGTH: 22
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 23 of human RB1 gene (xi) SEQUENCE DESCRIPTION: SEQ ID NO:23:

AATCTAATGT AATGGGTCCA CC                                          22

(2) INFORMATION FOR SEQ ID NO:24:

(i) SEQUENCE CHARACTERISTICS:
        (A) LENGTH: 22
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 23 of human RB1 gene (xi) SEQUENCE DESCRIPTION: SEQ ID NO:24:

ATCAAAATAA TCCCCCTCTC AT                22

(2) INFORMATION FOR SEQ ID NO:25:

(i) SEQUENCE CHARACTERISTICS:
        (A) LENGTH: 20
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 6 of human RB1 gene (xi) SEQUENCE DESCRIPTION: SEQ ID NO:25:

AAAGAAACAC CCAAAAGATA                20

(2) INFORMATION FOR SEQ ID NO:26:

(i) SEQUENCE CHARACTERISTICS:
        (A) LENGTH: 22
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 6 of human RB1 gene (xi) SEQUENCE DESCRIPTION: SEQ ID NO:26:

TAATAAGCCA AGCAGAGAAT GA                22

(2) INFORMATION FOR SEQ ID NO:27:

(i) SEQUENCE CHARACTERISTICS:
        (A) LENGTH: 22
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 7 of human RB1 gene (xi) SEQUENCE DESCRIPTION: SEQ ID NO:27:

TTATGGATAT ACTCTACCCT GC                                            22

(2) INFORMATION FOR SEQ ID NO:28:

(i) SEQUENCE CHARACTERISTICS:
            (A) LENGTH: 22
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
            (A) ORGANISM: human (ix) FEATURE:
            (A) NAME/KEY: primer for exon 7 of human RB1 gene (xi) SEQUENCE DESCRIPTION: SEQ ID NO:28:

CCTCCATTTG TTGTATTTTG AC                                            22

(2) INFORMATION FOR SEQ ID NO:29:

(i) SEQUENCE CHARACTERISTICS:
            (A) LENGTH: 20
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
            (A) ORGANISM: human (ix) FEATURE:
            (A) NAME/KEY: primer for exon 9 of human RB1 gene (xi) SEQUENCE DESCRIPTION: SEQ ID NO:29:

TCAAGAGTCA AGAGATTAGA                                               20

(2) INFORMATION FOR SEQ ID NO:30:

(i) SEQUENCE CHARACTERISTICS:
            (A) LENGTH: 22
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
            (A) ORGANISM: human (ix) FEATURE:
        (A) NAME/KEY: primer for exon 9 of human RB1 gene (xi) SEQUENCE DESCRIPTION: SEQ ID NO:30:

ATTATCCTCC CTCCACAGTC TC                                            22

(2) INFORMATION FOR SEQ ID NO:31:

(i) SEQUENCE CHARACTERISTICS:
        (A) LENGTH: 19
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 10 of human RB1 gene (xi) SEQUENCE DESCRIPTION: SEQ ID NO:31:

GTGCTGAGAG ATGTAATGA                                                19

(2) INFORMATION FOR SEQ ID NO:32:

(i) SEQUENCE CHARACTERISTICS:
        (A) LENGTH: 19
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 10 of human RB1 gene (xi) SEQUENCE DESCRIPTION: SEQ ID NO:32:

TATCTAAAGC AAATCAATC                                                19

(2) INFORMATION FOR SEQ ID NO:33:

(i) SEQUENCE CHARACTERISTICS:
        (A) LENGTH: 20
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:

(A) ORGANISM: human (ix) FEATURE:
    (A) NAME/KEY: primer for exon 11 of human RB1 gene (xi) SEQUENCE DESCRIPTION: SEQ ID NO:33:

TGAGACAACA GAAGCATTAT                                           20

(2) INFORMATION FOR SEQ ID NO:34:

(i) SEQUENCE CHARACTERISTICS:
        (A) LENGTH: 21
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 11 of human RB1 gene (xi) SEQUENCE DESCRIPTION: SEQ ID NO:34:

TGAACAAATC TGAAACACTA T                                         21

(2) INFORMATION FOR SEQ ID NO:35:

(i) SEQUENCE CHARACTERISTICS:
        (A) LENGTH: 22
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 12 of human RB1 gene (xi) SEQUENCE DESCRIPTION: SEQ ID NO:35:

CTCCCTTCAT TGCTTAACAC AT                                        22

(2) INFORMATION FOR SEQ ID NO:36:

(i) SEQUENCE CHARACTERISTICS:
        (A) LENGTH: 21
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
         (A) ORGANISM: human (ix) FEATURE:
         (A) NAME/KEY: primer for exon 12 of human RB1 gene (xi) SEQUENCE DESCRIPTION: SEQ ID NO:36:

AAAAGCAAGA AAAGATTATG G                                              21

(2) INFORMATION FOR SEQ ID NO:37:

(i) SEQUENCE CHARACTERISTICS:
        (A) LENGTH: 22
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
         (A) ORGANISM: human (ix) FEATURE:
         (A) NAME/KEY: primer for exon 27 of human RB1 gene (xi) SEQUENCE DESCRIPTION: SEQ ID NO:37:

ACTTACCCAG TACCATCAAT GC                                             22

(2) INFORMATION FOR SEQ ID NO:38:

(i) SEQUENCE CHARACTERISTICS:
        (A) LENGTH: 22
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
         (A) ORGANISM: human (ix) FEATURE:
         (A) NAME/KEY: primer for exon 27 of human RB1 gene (xi) SEQUENCE DESCRIPTION: SEQ ID NO:38:

TCAAGTGGCT TAGGAATCAC CC                                             22

(2) INFORMATION FOR SEQ ID NO:39:

(i) SEQUENCE CHARACTERISTICS:
        (A) LENGTH: 18
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
            (A) ORGANISM: human (ix) FEATURE:
            (A) NAME/KEY: primer for exon 4 of human RB1 gene (xi) SEQUENCE DESCRIPTION: SEQ ID NO:39:

TTGAAAACGA AATAACAC                                                       18

(2) INFORMATION FOR SEQ ID NO:40:

(i) SEQUENCE CHARACTERISTICS:
            (A) LENGTH: 22
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
            (A) ORGANISM: human (ix) FEATURE:
            (A) NAME/KEY: primer for exon 4 of human RB1 gene (xi) SEQUENCE DESCRIPTION: SEQ ID NO:40:

ATAAAAAATC AGAGTGTAAC CC                                                  22

(2) INFORMATION FOR SEQ ID NO:41:

(i) SEQUENCE CHARACTERISTICS:
            (A) LENGTH: 22
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
            (A) ORGANISM: human (ix) FEATURE:
            (A) NAME/KEY: primer for exon 14 of human RB1 gene (xi) SEQUENCE DESCRIPTION: SEQ ID NO:41:

GTGATTTTCT AAAATAGCAG GC                                                  22

(2) INFORMATION FOR SEQ ID NO:42:

(i) SEQUENCE CHARACTERISTICS:
            (A) LENGTH: 19
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
            (A) ORGANISM: human (ix) FEATURE:
            (A) NAME/KEY: primer for exon 14 of human RB1 gene (xi) SEQUENCE DESCRIPTION: SEQ ID NO:42:

CCAGGATGAT CTTGATGCC                                                          19

(2) INFORMATION FOR SEQ ID NO:43:

(i) SEQUENCE CHARACTERISTICS:
            (A) LENGTH: 22
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
            (A) ORGANISM: human (ix) FEATURE:
            (A) NAME/KEY: primer for exon 20 of human RB1 gene (xi) SEQUENCE DESCRIPTION: SEQ ID NO:43:

GAAAAGAGTG GTAGAAAAGA GG                                                      22

(2) INFORMATION FOR SEQ ID NO:44:

(i) SEQUENCE CHARACTERISTICS:
            (A) LENGTH: 22
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
            (A) ORGANISM: human (ix) FEATURE:
            (A) NAME/KEY: primer for exon 20 of human RB1 gene (xi) SEQUENCE DESCRIPTION: SEQ ID NO:44:

TAACAAGTAA GTAGGGAGGA GA                                                      22

(2) INFORMATION FOR SEQ ID NO:45:

(i) SEQUENCE CHARACTERISTICS:
            (A) LENGTH: 20
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
             (A) ORGANISM: human (ix) FEATURE:
             (A) NAME/KEY: primer for exon 24 of human RB1 gene (xi) SEQUENCE DESCRIPTION: SEQ ID NO:45:

GTATTTATGC TCATCTCTGC                                                    20

(2) INFORMATION FOR SEQ ID NO:46:

(i) SEQUENCE CHARACTERISTICS:
             (A) LENGTH: 22
             (B) TYPE: nucleic acid
             (C) STRANDEDNESS: single
             (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
             (A) ORGANISM: human (ix) FEATURE:
             (A) NAME/KEY: primer for exon 24 of human RB1 gene (xi) SEQUENCE DESCRIPTION: SEQ ID NO:46:

GTGTTTGAAT AACTGCATTT GG                                                 22

(2) INFORMATION FOR SEQ ID NO:47:

(i) SEQUENCE CHARACTERISTICS:
             (A) LENGTH: 21
             (B) TYPE: nucleic acid
             (C) STRANDEDNESS: single
             (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
             (A) ORGANISM: human (ix) FEATURE:
             (A) NAME/KEY: primer for exon 26 of human RB1 gene (xi) SEQUENCE DESCRIPTION: SEQ ID NO:47:

CGAAAGCATC ATAGTTACTG G                                                  21

(2) INFORMATION FOR SEQ ID NO:48:

(i) SEQUENCE CHARACTERISTICS:
             (A) LENGTH: 22
             (B) TYPE: nucleic acid
             (C) STRANDEDNESS: single
             (D) TOPOLOGY: linear

```
        (ii) MOLECULE TYPE: genomic DNA (iii) HYPOTHETICAL: no (iv) ANTI-SENSE: no (v) FRAGMENT TYPE: internal (vi) ORIGINAL SOURCE:
             (A) ORGANISM: human (ix) FEATURE:
             (A) NAME/KEY: primer for exon 26 of human RB1 gene (xi) SEQUENCE DESCRIPTION: SEQ ID NO:48:

ATATAACGAA AAGACTTCTT GC                                              22

(2) INFORMATION FOR SEQ ID NO:49:

(i) SEQUENCE CHARACTERISTICS:
             (A) LENGTH: 22
             (B) TYPE: nucleic acid
             (C) STRANDEDNESS: single
             (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
             (A) ORGANISM: human (ix) FEATURE:
             (A) NAME/KEY: primer for exons 15 and 16 of human RB1 gene (xi) SEQUENCE DESCRIPTION: SEQ ID NO:49:

CAATGCTGAC ACAAATAAGG TT                                              22

(2) INFORMATION FOR SEQ ID NO:50:

(i) SEQUENCE CHARACTERISTICS:
             (A) LENGTH: 20
             (B) TYPE: nucleic acid
             (C) STRANDEDNESS: single
             (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
             (A) ORGANISM: human (ix) FEATURE:
             (A) NAME/KEY: primer for exons 15 and 16 of human RB1 gene (xi) SEQUENCE DESCRIPTION: SEQ ID NO:50:

CCCCCGACCA AAGAAACACA                                                 20

(2) INFORMATION FOR SEQ ID NO:51:

(i) SEQUENCE CHARACTERISTICS:
             (A) LENGTH: 22
             (B) TYPE: nucleic acid
```

-continued (C) STRANDEDNESS: single
            (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
            (A) ORGANISM: human (ix) FEATURE:
            (A) NAME/KEY: primer for exon 17 of human RB1 gene (xi) SEQUENCE DESCRIPTION: SEQ ID NO:51:

ACCTTTCTAC TGTTTTCTTT GT                                               22

(2) INFORMATION FOR SEQ ID NO:52:

(i) SEQUENCE CHARACTERISTICS:
            (A) LENGTH: 20
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
            (A) ORGANISM: human (ix) FEATURE:
            (A) NAME/KEY: primer for exon 17 of human RB1 gene (xi) SEQUENCE DESCRIPTION: SEQ ID NO:52:

AAACACCTCT CACTAACAAT                                                  20

(2) INFORMATION FOR SEQ ID NO:53:

(i) SEQUENCE CHARACTERISTICS:
            (A) LENGTH: 22
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
            (A) ORGANISM: human (ix) FEATURE:
            (A) NAME/KEY: primer for exon 19 of human RB1 gene (xi) SEQUENCE DESCRIPTION: SEQ ID NO:53:

TGTATAATCT GTGATTCTTA GC                                               22

(2) INFORMATION FOR SEQ ID NO:54:

(i) SEQUENCE CHARACTERISTICS:

```
        (A) LENGTH: 22
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 19 of human RB1 gene (xi) SEQUENCE DESCRIPTION: SEQ ID NO:54:

GCAACATTAT CATTTCCATT TT                                                22

(2) INFORMATION FOR SEQ ID NO:55:

(i) SEQUENCE CHARACTERISTICS:
        (A) LENGTH: 18
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for promoter region of human RB1 gene (xi) SEQUENCE DESCRIPTION: SEQ ID NO:55:

CCCACCAGAC TCTTTGTA                                                     18

(2) INFORMATION FOR SEQ ID NO:56:

(i) SEQUENCE CHARACTERISTICS:
        (A) LENGTH: 22
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for promoter region of human RB1 gene (xi) SEQUENCE DESCRIPTION: SEQ ID NO:56:

ACGTCCCCTG AGAAAAACCG GA                                                22

(2) INFORMATION FOR SEQ ID NO:57:
```

```
    (i) SEQUENCE CHARACTERISTICS:
        (A) LENGTH: 21
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 1 of human RB1 gene (xi) SEQUENCE DESCRIPTION: SEQ ID NO:57:

GCCCCAGTTC CCCACAGACG C                                              21

(2) INFORMATION FOR SEQ ID NO:58:

(i) SEQUENCE CHARACTERISTICS:
        (A) LENGTH: 22
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 2 of human RB1 gene (xi) SEQUENCE DESCRIPTION: SEQ ID NO:58:

TCCTCTGGGT AATGGAATTA TT                                             22

(2) INFORMATION FOR SEQ ID NO:59:

(i) SEQUENCE CHARACTERISTICS:
        (A) LENGTH: 22
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 4 of human RB1 gene (xi) SEQUENCE DESCRIPTION: SEQ ID NO:59:

AGTAGTGATT TGATGTAGAG CT                                             22
```

(2) INFORMATION FOR SEQ ID NO:60:

(i) SEQUENCE CHARACTERISTICS:
        (A) LENGTH: 23
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 4 of human RB1 gene (xi) SEQUENCE DESCRIPTION: SEQ ID NO:60:

ATCAAGATGT TTGAGATTAT TCC                                      23

(2) INFORMATION FOR SEQ ID NO:61:

(i) SEQUENCE CHARACTERISTICS:
        (A) LENGTH: 22
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 6 of human RB1 gene (xi) SEQUENCE DESCRIPTION: SEQ ID NO:61:

CACAAAAAGA AACACCCAAA AG                                       22

(2) INFORMATION FOR SEQ ID NO:62:

(i) SEQUENCE CHARACTERISTICS:
        (A) LENGTH: 22
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 7 of human RB1 gene (xi) SEQUENCE DESCRIPTION: SEQ ID NO:62:

```
TACTCTACCC TGCGATTTTC TC                                              22
```

(2) INFORMATION FOR SEQ ID NO:63:

(i) SEQUENCE CHARACTERISTICS:
        (A) LENGTH: 22
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 9 of human RB1 gene (xi) SEQUENCE DESCRIPTION: SEQ ID NO:63:

```
ATGGGGGATT GACACCTCTA AC                                              22
```

(2) INFORMATION FOR SEQ ID NO:64:

(i) SEQUENCE CHARACTERISTICS:
        (A) LENGTH: 20
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 10 of human RB1 gene (xi) SEQUENCE DESCRIPTION: SEQ ID NO:64:

```
TAATGAAATC TGTGCCTCTG                                                 20
```

(2) INFORMATION FOR SEQ ID NO:65:

(i) SEQUENCE CHARACTERISTICS:
        (A) LENGTH: 22
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 11 of human RB1 gene (xi) SEQUENCE DESCRIPTION: SEQ ID NO:65:

TATGATTTTA TGAGACAACA GA                                                    22

(2) INFORMATION FOR SEQ ID NO:66:

(i) SEQUENCE CHARACTERISTICS:
         (A) LENGTH: 21
         (B) TYPE: nucleic acid
         (C) STRANDEDNESS: single
         (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
         (A) ORGANISM: human (ix) FEATURE:
         (A) NAME/KEY: primer for exon 12 of human RB1 gene (xi) SEQUENCE DESCRIPTION: SEQ ID NO:66:

AACTTGGGAG ATTGAAAACA T                                                     21

(2) INFORMATION FOR SEQ ID NO:67:

(i) SEQUENCE CHARACTERISTICS:
         (A) LENGTH: 22
         (B) TYPE: nucleic acid
         (C) STRANDEDNESS: single
         (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
         (A) ORGANISM: human (ix) FEATURE:
         (A) NAME/KEY: primer for exon 14 of human RB1 gene (xi) SEQUENCE DESCRIPTION: SEQ ID NO:67:

AAAGCAGGAG GATCTCTTGA GC                                                    22

(2) INFORMATION FOR SEQ ID NO:68:

(i) SEQUENCE CHARACTERISTICS:
         (A) LENGTH: 21
         (B) TYPE: nucleic acid
         (C) STRANDEDNESS: single
         (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
         (A) ORGANISM: human (ix) FEATURE:

(A) NAME/KEY: primer for exons 15 and 16 of human RB1 gene (xi) SEQUENCE DESCRIPTION: SEQ ID NO:68:

CTCCCCCGAC CACCGAAACA C                                              21

(2) INFORMATION FOR SEQ ID NO:69:

(i) SEQUENCE CHARACTERISTICS:
        (A) LENGTH: 21
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 17 of human RB1 gene (xi) SEQUENCE DESCRIPTION: SEQ ID NO:69:

ATTAGATGGT TTAGGGTGCT C                                              21

(2) INFORMATION FOR SEQ ID NO:70:

(i) SEQUENCE CHARACTERISTICS:
        (A) LENGTH: 19
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 18 of human RB1 gene (xi) SEQUENCE DESCRIPTION: SEQ ID NO:70:

TTTTTGTGTG TGGGAAGTA                                                 19

(2) INFORMATION FOR SEQ ID NO:71:

(i) SEQUENCE CHARACTERISTICS:
        (A) LENGTH: 21
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human

```
        (ix) FEATURE:
              (A) NAME/KEY: primer for exon 19 of human RB1 gene (xi) SEQUENCE DESCRIPTION: SEQ ID NO:71:

ATGACAAGCA GTTTTCCTAT T                                                21

(2) INFORMATION FOR SEQ ID NO:72:

(i) SEQUENCE CHARACTERISTICS:
              (A) LENGTH: 22
              (B) TYPE: nucleic acid
              (C) STRANDEDNESS: single
              (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
              (A) ORGANISM: human (ix) FEATURE:
              (A) NAME/KEY: primer for exon 23 of human RB1 gene (xi) SEQUENCE DESCRIPTION: SEQ ID NO:72:

CCAGGGTAGG TCAAAAGTAT CC                                               22

(2) INFORMATION FOR SEQ ID NO:73:

(i) SEQUENCE CHARACTERISTICS:
              (A) LENGTH: 22
              (B) TYPE: nucleic acid
              (C) STRANDEDNESS: single
              (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
              (A) ORGANISM: human (ix) FEATURE:
              (A) NAME/KEY: primer for exon 24 of human RB1 gene (xi) SEQUENCE DESCRIPTION: SEQ ID NO:73:

ATGTATTTAT GCTCATCTCT GC                                               22

(2) INFORMATION FOR SEQ ID NO:74:

(i) SEQUENCE CHARACTERISTICS:
              (A) LENGTH: 22
              (B) TYPE: nucleic acid
              (C) STRANDEDNESS: single
              (D) TOPOLOGY: linear (ii) MOLECULE TYPE: genomic DNA (iii) HYPOTHETICAL: no (iv) ANTI-SENSE: no (v) FRAGMENT TYPE: internal
```

(vi) ORIGINAL SOURCE:
            (A) ORGANISM: human (ix) FEATURE:
            (A) NAME/KEY: primer for exon 26 of human RB1 gene (xi) SEQUENCE DESCRIPTION: SEQ ID NO:74:

TCGAAAGCAT CARAGTTACT GG                                                22

(2) INFORMATION FOR SEQ ID NO:75:

(i) SEQUENCE CHARACTERISTICS:
            (A) LENGTH: 22
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
            (A) ORGANISM: human (ix) FEATURE:
            (A) NAME/KEY: primer for promoter region of human RB1 gene (xi) SEQUENCE DESCRIPTION: SEQ ID NO:75:

ACAGTCACCC ACCAGACTCT TT                                                22

(2) INFORMATION FOR SEQ ID NO:76:

(i) SEQUENCE CHARACTERISTICS:
            (A) LENGTH: 19
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
            (A) ORGANISM: human (ix) FEATURE:
            (A) NAME/KEY: primer for exon 1 of human RB1 gene (xi) SEQUENCE DESCRIPTION: SEQ ID NO:76:

CGCCCGCCCT ACGCACACC                                                    19

(2) INFORMATION FOR SEQ ID NO:77:

(i) SEQUENCE CHARACTERISTICS:
            (A) LENGTH: 17
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
           (A) ORGANISM: human (ix) FEATURE:
           (A) NAME/KEY: primer for exon 1 of human RB1 gene (xi) SEQUENCE DESCRIPTION: SEQ ID NO:77:

CGTGAGCGCG GGCGGAA                                              17

(2) INFORMATION FOR SEQ ID NO:78:

(i) SEQUENCE CHARACTERISTICS:
           (A) LENGTH: 18
           (B) TYPE: nucleic acid
           (C) STRANDEDNESS: single
           (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
           (A) ORGANISM: human (ix) FEATURE:
           (A) NAME/KEY: primer for exon 2 of human RB1 gene (xi) SEQUENCE DESCRIPTION: SEQ ID NO:78:

TAGTGATTTG AAGTTGTT                                             18

(2) INFORMATION FOR SEQ ID NO:79:

(i) SEQUENCE CHARACTERISTICS:
           (A) LENGTH: 18
           (B) TYPE: nucleic acid
           (C) STRANDEDNESS: single
           (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
           (A) ORGANISM: human (ix) FEATURE:
           (A) NAME/KEY: primer for exon 2 of human RB1 gene (xi) SEQUENCE DESCRIPTION: SEQ ID NO:79:

ATGTGCAAAC TATTGAAA                                             18

(2) INFORMATION FOR SEQ ID NO:80:

(i) SEQUENCE CHARACTERISTICS:
           (A) LENGTH: 22
           (B) TYPE: nucleic acid
           (C) STRANDEDNESS: single
           (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
           (A) ORGANISM: human (ix) FEATURE:
           (A) NAME/KEY: primer for exon 3 of human RB1 gene (xi) SEQUENCE DESCRIPTION: SEQ ID NO:80:

CTATTGAGAG GAAAATCCAG AA                                                22

(2) INFORMATION FOR SEQ ID NO:81:

(i) SEQUENCE CHARACTERISTICS:
           (A) LENGTH: 21
           (B) TYPE: nucleic acid
           (C) STRANDEDNESS: single
           (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
           (A) ORGANISM: human (ix) FEATURE:
           (A) NAME/KEY: primer for exon 3 of human RB1 gene (xi) SEQUENCE DESCRIPTION: SEQ ID NO:81:

TAACATAGTA GTATCCAGTG T                                                 21

(2) INFORMATION FOR SEQ ID NO:82:

(i) SEQUENCE CHARACTERISTICS:
           (A) LENGTH: 18
           (B) TYPE: nucleic acid
           (C) STRANDEDNESS: single
           (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
           (A) ORGANISM: human (ix) FEATURE:
           (A) NAME/KEY: primer for exon 4 of human RB1 gene (xi) SEQUENCE DESCRIPTION: SEQ ID NO:82:

ATCAGAGTGA AACCCTAA                                                     18

(2) INFORMATION FOR SEQ ID NO:83:

(i) SEQUENCE CHARACTERISTICS:
           (A) LENGTH: 20
           (B) TYPE: nucleic acid
           (C) STRANDEDNESS: single
           (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
              (A) ORGANISM: human (ix) FEATURE:
              (A) NAME/KEY: primer for exon 5 of human RB1 gene (xi) SEQUENCE DESCRIPTION: SEQ ID NO:83:

AGATGTTTGA GATTATTCCA                                                  20

(2) INFORMATION FOR SEQ ID NO:84:

(i) SEQUENCE CHARACTERISTICS:
              (A) LENGTH: 20
              (B) TYPE: nucleic acid
              (C) STRANDEDNESS: single
              (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
              (A) ORGANISM: human (ix) FEATURE:
              (A) NAME/KEY: primer for exon 5 of human RB1 gene (xi) SEQUENCE DESCRIPTION: SEQ ID NO:84:

TAAATTACGA AAAAATGTTA                                                  20

(2) INFORMATION FOR SEQ ID NO:85:

(i) SEQUENCE CHARACTERISTICS:
              (A) LENGTH: 20
              (B) TYPE: nucleic acid
              (C) STRANDEDNESS: single
              (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
              (A) ORGANISM: human (ix) FEATURE:
              (A) NAME/KEY: primer for exon 6 of human RB1 gene (xi) SEQUENCE DESCRIPTION: SEQ ID NO:85:

CAGAGAATGA GGGAGGAGTA                                                  20

(2) INFORMATION FOR SEQ ID NO:86:

(i) SEQUENCE CHARACTERISTICS:
              (A) LENGTH: 20
              (B) TYPE: nucleic acid
              (C) STRANDEDNESS: single
              (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
             (A) ORGANISM: human (ix) FEATURE:
             (A) NAME/KEY: primer for exon 7 of human RB1 gene (xi) SEQUENCE DESCRIPTION: SEQ ID NO:86:

TGTCTTATCT TTCCTTCTAT                                                  20

(2) INFORMATION FOR SEQ ID NO:87:

(i) SEQUENCE CHARACTERISTICS:
             (A) LENGTH: 20
             (B) TYPE: nucleic acid
             (C) STRANDEDNESS: single
             (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
             (A) ORGANISM: human (ix) FEATURE:
             (A) NAME/KEY: primer for exon 7 of human RB1 gene (xi) SEQUENCE DESCRIPTION: SEQ ID NO:87:

TGCGATTTTC TCTCATACAA                                                  20

(2) INFORMATION FOR SEQ ID NO:88:

(i) SEQUENCE CHARACTERISTICS:
             (A) LENGTH: 19
             (B) TYPE: nucleic acid
             (C) STRANDEDNESS: single
             (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
             (A) ORGANISM: human (ix) FEATURE:
             (A) NAME/KEY: primer for exon 8 of human RB1 gene (xi) SEQUENCE DESCRIPTION: SEQ ID NO:88:

CATAACAAAA GAAGTAAAT                                                   19

(2) INFORMATION FOR SEQ ID NO:89:

(i) SEQUENCE CHARACTERISTICS:
             (A) LENGTH: 19
             (B) TYPE: nucleic acid
             (C) STRANDEDNESS: single (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
            (A) ORGANISM: human (ix) FEATURE:
            (A) NAME/KEY: primer for exon 8 of human RB1 gene (xi) SEQUENCE DESCRIPTION: SEQ ID NO:89:

ATGTTACCAA GATTATTTT                                                  19

(2) INFORMATION FOR SEQ ID NO:90:

(i) SEQUENCE CHARACTERISTICS:
            (A) LENGTH: 20
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
            (A) ORGANISM: human (ix) FEATURE:
            (A) NAME/KEY: primer for exon 9 of human RB1 gene (xi) SEQUENCE DESCRIPTION: SEQ ID NO:90:

TCCACAGTCT CAAAACATTA                                                 20

(2) INFORMATION FOR SEQ ID NO:91:

(i) SEQUENCE CHARACTERISTICS:
            (A) LENGTH: 19
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
            (A) ORGANISM: human (ix) FEATURE:
            (A) NAME/KEY: primer for exon 10 of human RB1 gene (xi) SEQUENCE DESCRIPTION: SEQ ID NO:91:

TATCTAAAGC AAATCAATC                                                  19

(2) INFORMATION FOR SEQ ID NO:92:

(i) SEQUENCE CHARACTERISTICS:
            (A) LENGTH: 18

```
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
            (A) ORGANISM: human (ix) FEATURE:
            (A) NAME/KEY: primer for exon 11 of human RB1 gene (xi) SEQUENCE DESCRIPTION: SEQ ID NO:92:

AATCTGAAAC ACTATAAA                                                   18

(2) INFORMATION FOR SEQ ID NO:93:

(i) SEQUENCE CHARACTERISTICS:
            (A) LENGTH: 19
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
            (A) ORGANISM: human (ix) FEATURE:
            (A) NAME/KEY: primer for exon 12 of human RB1 gene (xi) SEQUENCE DESCRIPTION: SEQ ID NO:93:

TGTTAGATAG GAGATTAGT                                                  19

(2) INFORMATION FOR SEQ ID NO:94:

(i) SEQUENCE CHARACTERISTICS:
            (A) LENGTH: 18
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
            (A) ORGANISM: human (ix) FEATURE:
            (A) NAME/KEY: primer for exon 12 of human RB1 gene (xi) SEQUENCE DESCRIPTION: SEQ ID NO:94:

CCCTTCATTG CTTAACAC                                                   18

(2) INFORMATION FOR SEQ ID NO:95:
```

(i) SEQUENCE CHARACTERISTICS:
        (A) LENGTH: 18
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 13 of human RB1 gene (xi) SEQUENCE DESCRIPTION: SEQ ID NO:95:

TCTGATTAGA CAGTATCC                                            18

(2) INFORMATION FOR SEQ ID NO:96:

(i) SEQUENCE CHARACTERISTICS:
        (A) LENGTH: 18
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 13 of human RB1 gene (xi) SEQUENCE DESCRIPTION: SEQ ID NO:96:

GAACTGGAAA GATGCTGC                                            18

(2) INFORMATION FOR SEQ ID NO:97:

(i) SEQUENCE CHARACTERISTICS:
        (A) LENGTH: 18
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 14 of human RB1 gene (xi) SEQUENCE DESCRIPTION: SEQ ID NO:97:

TCTTGATGCC TTGACCTC                                            18

(2) INFORMATION FOR SEQ ID NO:98:

(i) SEQUENCE CHARACTERISTICS:
        (A) LENGTH: 20
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exonS 15 AND 16 of human RB1 gene (xi) SEQUENCE DESCRIPTION: SEQ ID NO:98:

ATACTTACTT CTATAAAAAG                                                          20

(2) INFORMATION FOR SEQ ID NO:99:

(i) SEQUENCE CHARACTERISTICS:
        (A) LENGTH: 20
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exonS 15 AND 16 of human RB1 gene (xi) SEQUENCE DESCRIPTION: SEQ ID NO:99:

CCAAAGAAAC ACACCACATT                                                          20

(2) INFORMATION FOR SEQ ID NO:100:

(i) SEQUENCE CHARACTERISTICS:
        (A) LENGTH: 20
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 17 of human RB1 gene (xi) SEQUENCE DESCRIPTION: SEQ ID NO:100:

CTGATAATAA CTTCCAAAAA                                                          20

(2) INFORMATION FOR SEQ ID NO:101:

(i) SEQUENCE CHARACTERISTICS:
        (A) LENGTH: 18
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 18 of human RB1 gene (xi) SEQUENCE DESCRIPTION: SEQ ID NO:101:

TCCCTACAGT TTCTTTAT                                              18

(2) INFORMATION FOR SEQ ID NO:102:

(i) SEQUENCE CHARACTERISTICS:
        (A) LENGTH: 18
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 18 of human RB1 gene (xi) SEQUENCE DESCRIPTION: SEQ ID NO:102:

TTTGATATGT ACCTGGGA                                              18

(2) INFORMATION FOR SEQ ID NO:103:

(i) SEQUENCE CHARACTERISTICS:
        (A) LENGTH: 18
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 19 of human RB1 gene (xi) SEQUENCE DESCRIPTION: SEQ ID NO:103:

```
GATGAGGAAA CTGAGACA                                                   18

(2) INFORMATION FOR SEQ ID NO:104:

(i) SEQUENCE CHARACTERISTICS:
        (A) LENGTH: 18
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 19 of human RB1 gene (xi) SEQUENCE DESCRIPTION: SEQ ID NO:104:

GTGATTCTTA GCCAACTT                                                   18

(2) INFORMATION FOR SEQ ID NO:105:

(i) SEQUENCE CHARACTERISTICS:
        (A) LENGTH: 20
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 20 of human RB1 gene (xi) SEQUENCE DESCRIPTION: SEQ ID NO:105:

AGTAGGGAGG AGAGAAGGTG                                                 20

(2) INFORMATION FOR SEQ ID NO:106:

(i) SEQUENCE CHARACTERISTICS:
        (A) LENGTH: 20
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 20 of human RB1 gene
```

(xi) SEQUENCE DESCRIPTION: SEQ ID NO:106:

CAAAATGAAC AGTAAAAATG                                                    20

(2) INFORMATION FOR SEQ ID NO:107:

(i) SEQUENCE CHARACTERISTICS:
            (A) LENGTH: 18
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
            (A) ORGANISM: human (ix) FEATURE:
            (A) NAME/KEY: primer for exon 21 of human RB1 gene (xi) SEQUENCE DESCRIPTION: SEQ ID NO:107:

CTATGTTATG TTATGGAT                                                      18

(2) INFORMATION FOR SEQ ID NO:108:

(i) SEQUENCE CHARACTERISTICS:
            (A) LENGTH: 18
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
            (A) ORGANISM: human (ix) FEATURE:
            (A) NAME/KEY: primer for exon 21 of human RB1 gene (xi) SEQUENCE DESCRIPTION: SEQ ID NO:108:

AAAGAAAGAA AATGGTAT                                                      18

(2) INFORMATION FOR SEQ ID NO:109:

(i) SEQUENCE CHARACTERISTICS:
            (A) LENGTH: 18
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
            (A) ORGANISM: human (ix) FEATURE:
        (A) NAME/KEY: primer for exon 22 of human RB1 gene (xi) SEQUENCE DESCRIPTION: SEQ ID NO:109:

TGGTGGACCC ATTACATT                                                         18

(2) INFORMATION FOR SEQ ID NO:110:

(i) SEQUENCE CHARACTERISTICS:
        (A) LENGTH: 18
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 22 of human RB1 gene (xi) SEQUENCE DESCRIPTION: SEQ ID NO:110:

ACCAGTCAAA AAGTATTA                                                         18

(2) INFORMATION FOR SEQ ID NO:111:

(i) SEQUENCE CHARACTERISTICS:
        (A) LENGTH: 18
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 23 of human RB1 gene (xi) SEQUENCE DESCRIPTION: SEQ ID NO:111:

TCTCATTCTT TACTACTT                                                         18

(2) INFORMATION FOR SEQ ID NO:112:

(i) SEQUENCE CHARACTERISTICS:
        (A) LENGTH: 18
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:

(A) ORGANISM: human (ix) FEATURE:
        (A) NAME/KEY: primer for exon 23 of human RB1 gene (xi) SEQUENCE DESCRIPTION: SEQ ID NO:112:

TTGGAAAAAT CTAATGTA                                                      18

(2) INFORMATION FOR SEQ ID NO:113:

(i) SEQUENCE CHARACTERISTICS:
        (A) LENGTH: 18
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 24 of human RB1 gene (xi) SEQUENCE DESCRIPTION: SEQ ID NO:113:

CTTTTATACT TACAATGC                                                      18

(2) INFORMATION FOR SEQ ID NO:114:

(i) SEQUENCE CHARACTERISTICS:
        (A) LENGTH: 18
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 24 of human RB1 gene (xi) SEQUENCE DESCRIPTION: SEQ ID NO:114:

TATGGTTTTT TATTACTA                                                      18

(2) INFORMATION FOR SEQ ID NO:115:

(i) SEQUENCE CHARACTERISTICS:
        (A) LENGTH: 18
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal

```
        (vi) ORIGINAL SOURCE:
              (A) ORGANISM: human (ix) FEATURE:
              (A) NAME/KEY: primer for exon 25 of human RB1 gene (xi) SEQUENCE DESCRIPTION: SEQ ID NO:115:

ATGACCATCT CAGCTACT                                                   18

(2) INFORMATION FOR SEQ ID NO:116:

(i) SEQUENCE CHARACTERISTICS:
              (A) LENGTH: 19
              (B) TYPE: nucleic acid
              (C) STRANDEDNESS: single
              (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
              (A) ORGANISM: human (ix) FEATURE:
              (A) NAME/KEY: primer for exon 25 of human RB1 gene (xi) SEQUENCE DESCRIPTION: SEQ ID NO:116:

TTGCTAACTA TGAAACACT                                                  19

(2) INFORMATION FOR SEQ ID NO:117:

(i) SEQUENCE CHARACTERISTICS:
              (A) LENGTH: 18
              (B) TYPE: nucleic acid
              (C) STRANDEDNESS: single
              (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
              (A) ORGANISM: human (ix) FEATURE:
              (A) NAME/KEY: primer for exon 26 of human RB1 gene (xi) SEQUENCE DESCRIPTION: SEQ ID NO:117:

ATTGTTTATT TCGTTTAC                                                   18

(2) INFORMATION FOR SEQ ID NO:118:

(i) SEQUENCE CHARACTERISTICS:
              (A) LENGTH: 18
              (B) TYPE: nucleic acid
              (C) STRANDEDNESS: single
              (D) TOPOLOGY: linear (ii) MOLECULE TYPE: genomic DNA (iii) HYPOTHETICAL: no (iv) ANTI-SENSE: no
```

(v) FRAGMENT TYPE: internal (vi) ORIGINAL SOURCE:
            (A) ORGANISM: human (ix) FEATURE:
            (A) NAME/KEY: primer for exon 26 of human RB1 gene (xi) SEQUENCE DESCRIPTION: SEQ ID NO:118:

ATTTGAGTTT TCCATTTA                                                        18

(2) INFORMATION FOR SEQ ID NO:119:

(i) SEQUENCE CHARACTERISTICS:
            (A) LENGTH: 19
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
            (A) ORGANISM: human (ix) FEATURE:
            (A) NAME/KEY: primer for exon 27 of human RB1 gene (xi) SEQUENCE DESCRIPTION: SEQ ID NO:119:

CTTAGGAATC ACCCAAACA                                                       19

(2) INFORMATION FOR SEQ ID NO:120:

(i) SEQUENCE CHARACTERISTICS:
            (A) LENGTH: 19
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
            (A) ORGANISM: human (ix) FEATURE:
            (A) NAME/KEY: primer for exon 27 of human RB1 gene (xi) SEQUENCE DESCRIPTION: SEQ ID NO:120:

AGTACCATCA ATGCTGTTA                                                       19

(2) INFORMATION FOR SEQ ID NO:121:

(i) SEQUENCE CHARACTERISTICS:
            (A) LENGTH: 19
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
            (A) ORGANISM: human (ix) FEATURE:
            (A) NAME/KEY: primer for promoter region of human RB1 gene (xi) SEQUENCE DESCRIPTION: SEQ ID NO:121:

CTGAGAAAAA CCGGACGCG                                                    19

(2) INFORMATION FOR SEQ ID NO:122:

(i) SEQUENCE CHARACTERISTICS:
            (A) LENGTH: 20
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
            (A) ORGANISM: human (ix) FEATURE:
            (A) NAME/KEY: primer for exon 4 of human RB1 gene (xi) SEQUENCE DESCRIPTION: SEQ ID NO:122:

ATATAGTAGT GATTTGATGT                                                   20

(2) INFORMATION FOR SEQ ID NO:123:

(i) SEQUENCE CHARACTERISTICS:
            (A) LENGTH: 20
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
            (A) ORGANISM: human (ix) FEATURE:
            (A) NAME/KEY: primer for exon 4 of human RB1 gene (xi) SEQUENCE DESCRIPTION: SEQ ID NO:123:

ATGACATAAA AAATCAGAGT                                                   20

METHOD, REAGENTS AND KIT FOR DIAGNOSIS AND TARGETED SCREENING FOR RETINOBLASTOMA

This application is a continuation of International Patent Application No. PCT/US95/08604 filed Jul. 7, 1995 designating the United States, which is a continuation of U.S. patent appication Ser. No. 08/271,942 filed Jul. 8, 1994, now U.S. Pat. No. 5,550,020.

BACKGROUND OF THE INVENTION

This application relates to a method, reagents and kits for diagnosis and targeted screening for retinoblastoma.

Retinoblastoma is a form of cancer affecting the eyes of young children. It results from mutations in the RB1 gene that lead to the loss of functional RB protein in the retinoblasts of the fetal and juvenile eye. Because the RB protein is involved in the control mechanism for proteins or peptides that promote cell division, cells lacking in functional RB protein undergo unregulated division, leading to the formation of a tumor within the eye.

The impact of the tumor within the eye depends in large part on the size of the tumor when detected. If the tumor is very large, it may be necessary to remove the eye completely. Smaller tumors may be treated with techniques such as photocoagulation, cryotherapy or radiation, making it possible to save visual function, although treatment with radiation, which is necessary in more advanced cases, increases the risk of subsequent tumor formation. It is thus very important to the prognosis of the patient to detect retinoblastoma early on. Unfortunately, retinoblastoma is not accompanied by any readily identified early symptoms, nor is there a blood test which can be routinely administered to screen for the disease. For this reason, most early detection of retinoblastoma occurs only when one member of a family has already been diagnosed as having retinoblastoma.

The accepted procedure which is currently followed after a diagnosis of retinoblastoma in one child of a family is to carefully monitor that child's siblings and first cousins during the period of significant risk, i.e., generally through about age seven. This monitoring, which involves frequent doctor visits, and frequently includes examination under anesthesia, is very costly. It would therefore be desirable to have a mechanism for determining the genetic basis for any given child's tumors, to be more fully able to assess which of the child's siblings and other relatives are actually at risk, and to permit genetic testing of potentially-at-risk individuals to limit monitoring to those actually at risk.

In addition, it has been determined that in some cases, ovarian cancer and breast cancer may have an associated-mutation in the RB1 gene. Since the presence of such a mutation may provide indications as to the most appropriate treatment regimen for the ovarian or breast cancer, the testing of breast and ovarian cancer biopsy samples for mutations in the RB1 gene may also be desirable.

Mechanisms for genetic testing for retinoblastoma have been previously proposed. For example, RNase protection of the mRNA of retinoblastoma is able to detect about 70% of mutations to the RB1 gene, but is dependent on the existence of retinoblastoma tumor mRNA. Dunn et al., Science 241: 1797 (1988); Dunn et al., Mol. Cell. Biol. 9: 4594 (1989). Complete sequencing of each exon might also be performed as described by Yandell et al., N. Engl. J. Med. 321: 1689 (1989), but the cost associated with this approach using existing technology is prohibitive. Because of this cost factor, it was previously suggested that the exons of the RB1 molecule could be screened using mobility differences as described in Orita et al., Proc. Nat'l Acad. Sci. U.S.A. 86: 2766 (1989) so that only those believed to contain a mutation would be sequenced. Gallie, B. L., "The Misadventures of RB1" in Causes and Consequences of Chromosomal Aberrations, pp 429–446, CRC Press (1993).

Unfortunately, despite its early promise, the use of exon screening based on mobility differences followed by selective exon sequencing has proven unreliable for providing diagnostic and targeted screening results concerning retinoblastoma. Thus, there is still no cost effective and reliable test which can be performed on individuals diagnosed with retinoblastoma and their juvenile relations to eliminate unneeded physical examinations. It is an object of the present invention to provide such a test.

SUMMARY OF THE INVENTION

In accordance with the present invention, reliable and cost effective testing for mutations in the RB1 gene can be achieved by
  (a) quantitatively amplifying exons of the sample RB1 gene using primers complementary to intron regions flanking each exon;
  (b) determining the lengths or quantity of the amplification products for each exon amplified and comparing that length or quantity to the length or quantity of amplification products obtained when a wild-type RB1 gene is amplified using the same primers, whereby differences in length between an amplified sample exon and the corresponding amplified wild-type exon reflect the occurrence of an insertion or deletion mutation in the sample RB1 gene; and
  (c) determining the nucleic acid sequence of each exon found to contain an insertion or deletion mutation, or of all exons in the event no insertion or deletion mutations are identified. Preferably, the amplification of the exons is multiplexed so that more than one exon is amplified in a single vessel using sets of primers which provide gene fragments of distinctive lengths when used to amplify a normal RB1 gene.

The information obtained in the test is used to generate a report which is used to provide appropriate genetic counseling to the family of individuals diagnosed with retinoblastoma. The generation of such reports, which may be in the form of a printed report, an electronic communication, such as a facsimile or electronic mail (e-mail) transmission, or a posting of a data entry in a computer record relating to the patient, is a further aspect of the present invention.

In order to practice the method of the present invention, it was necessary to develop a multitude of primers for amplification. These primers, taken individually or as part of kits for detection of RB1 mutations represent a further aspect of the present invention. Particularly preferred primers constitute sets that are compatible for coamplification and that produce amplified gene fragments of distinctive length from primers for other exons within the same set.

DETAILED DESCRIPTION OF THE INVENTION

The present invention relates to a method for the identification of mutations in the RB1 gene, method for generating reports and providing family counseling to relatives of patients with RB1 mutations, and to oligonucleotide primers and kits useful in practicing these methods.

The method for identification of mutations in the RB1 gene is based upon a hierarchical approach in which a sample derived from a patient diagnosed with retinoblastoma is first tested with a test of moderate accuracy but high specificity, that is a test which detects about 50% of all mutations (i.e., about 50% false negatives), but essentially never gives a false positive reading. A sample which exhibits a negative result is thereafter subjected to a more costly, but more accurate test to determine if a mutation is present. By eliminating this test from over half of the samples, however, the average cost of the test goes down without sacrificing analytical performance. This hierarchical approach is an example of a more general method which is described in U.S. Pat. No. 5,545,527 and International Patent Publication No. WO 96/07761, which are incorporated herein by reference.

Figure 1:
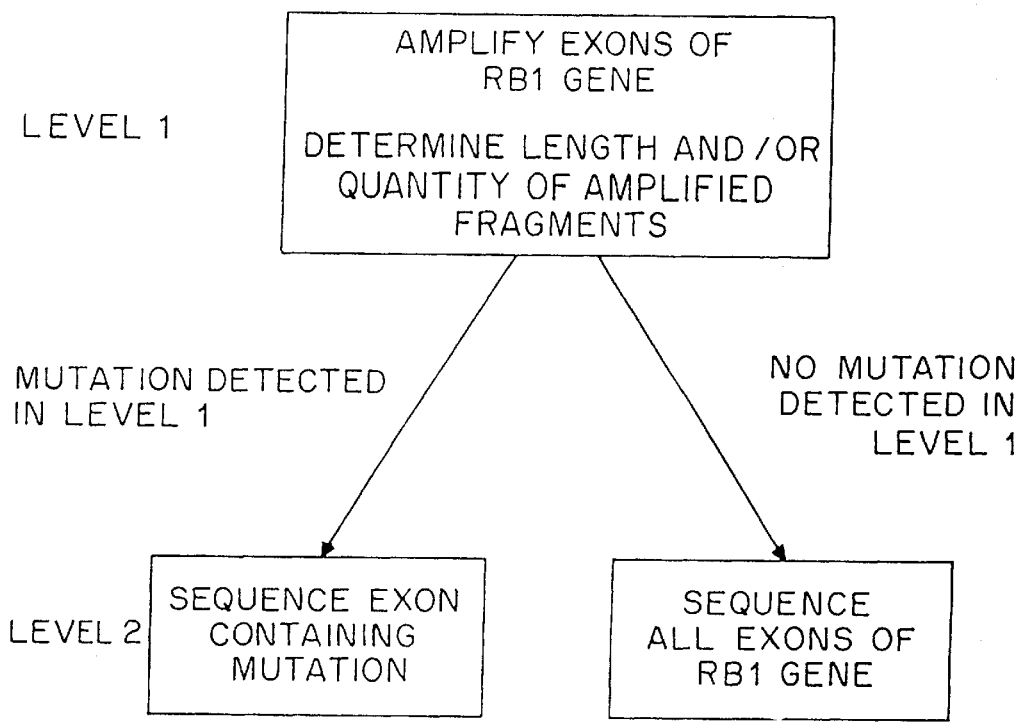
FIG. 1 shows a schematic representation of the hierarchical analysis method for identification of mutations in the RB1 gene in accordance with the present invention.

In the case of testing for mutations in the RB1 gene, the hierarchy preferably consists of two levels. Level 1, as shown in FIG. 1, involves a test performed on all patient samples. In this test, one or more exons of the RB1 gene are individually quantitatively amplified and the lengths and/or quantity of the amplified fragments are determined. If there is a variance between the length of any amplified exon, and the normal length of that exon, this is an indication of an insertion or deletion mutation in that exon. The quantity of amplified material from amplification of a sample exon may also reflect the loss of genetic material. In particular, by comparing the quantity of amplified materials produced to standards amplified from a null allele (0 copies of RB1), a hemizygous standard (1 copy of RB1), a wild type standard (2 copies of RB1) and a trisomy standard (3 copies of RB1) the nature of a mutation may be further investigated.

The number of exons tested in Level 1 of the hierarchy is a matter of choice for the user. For example, it has been observed that disease-associated mutations in the RB1 gene rarely occur in exons 5, 25, 26 and 27. It may therefore be desirable to test these exons last, after testing other exons to see if a mutation sufficient to cause the disease is detected, before incurring the expense to test these less likely exons. In testing these other exons, the user may choose to test them one at a time, or in one multiplexing group at a time. Alternatively, the user may choose to test all exons simultaneously at the first level of the hierarchy.

When a mutation is detected in level one of the hierarchy, it is not necessary to perform additional tests on the patient sample to complete the identification process. Preferably, however, the sequence of the mutated exon will be determined as part of the second level of the hierarchy to confirm that the mutation detected can in fact be a cause of the observed disease.

Figure 2:
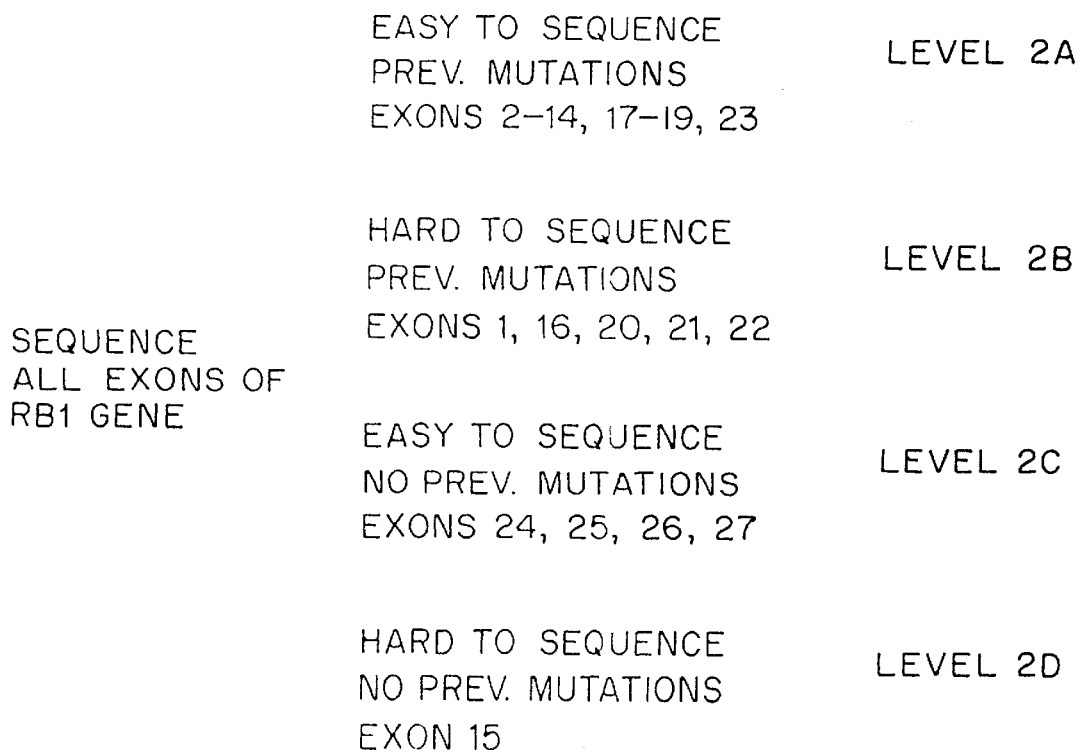
FIG. 2 shows a sub-hierarchy useful in the sequencing step of the method of the invention.

If no mutation is detected in the first level of testing, the second level of tests is performed. This involves determining the sequence of the exons to locate the mutation. Sequencing is expensive, however, and so it may be desirable to use a sub-hierarchy within this level of testing to reduce the likelihood of having to sequence all of the exons. In this case, a suitable sub-hierarchy is shown in FIG. 2. In accordance with this sub-hierarchy, the first exons sequenced (Level 2A) are those which are easy to sequence and which have been the site of other disease-associated mutations. Next, if no mutation which could result in retinoblastoma is found, exons are sequenced which are hard to sequence and which have been the site of other disease-associated mutations (Level 2B). The third level of the sub-hierarchy includes exons which are easy to sequence but which have never been shown to contain a disease-associated mutation (Level 2C). Finally, exons are sequenced which are hard to sequence but which have never been shown to contain a disease-associated mutation (Level 2D).

The primers used to amplify the sample DNA for the first test in the hierarchy are oligonucleotides of defined sequence selected to hybridize selectively with particular portions of the RB1 gene. Each primer has bound to it a detectable label. A preferred example of such a label is fluorescein, which is a standard label used in nucleic acid sequencing systems using laser light as a detection system. Other detectable labels can also be employed, however, including other fluorophores, radio-labels, chemical couplers such as biotin which can be detected with streptavidin-linked enzymes, and epitope tags such as digoxigenin detected using antibodies available from Boehringer-Mannheim.

While considerable variation is possible in the sequence of the primers used in amplifying the exons during the first step in the method of the present invention, the primers used in amplification and the conditions of the amplification are preferably optimized for use in the present invention. Looking first at the primers used, it will be understood that in order to avoid the possibility of false positive results the primer pair, i.e., the combination of the 5'-primer and the 3'-primer for any given exon must be unique to the RB1 gene so that only the RB1 gene will be amplified. This means that the primer sequences will be generally somewhat longer than the minimum which can be used as an amplification primer. Preferred primers are from 18 to 23 nucleotides in length, without internal homology or primer-primer homology. It is also desirable for the primers to form more stable duplexes with the target DNA at the primer's 5'-ends than at their 3'-ends, because this leads to less false priming. Stability can be approximated by GC content, since GC base pairs are more stable than AT pairs, or by nearest neighbor thermodynamic parameters. Breslauer et al., "Predicting DNA duplex stability from base sequence", *Proc. Nat'l Acad. Sci. USA* 83: 3746–3750 (1986). In addition, to ensure complete amplification of each exon, the two primers of a pair are preferably selected to hybridize in the introns immediately flanking the exon to be amplified using the primer pair.

Additional factors apply to the selection of primers for multiplexed amplification of exons. These factors are discussed in Rylchik, W., Selection of Primers for Polymerase Chain Reaction", in *Methods in Molecular Biology, Vol. 15: PCR Protocols: Current Methods and Applications*, White, B. A. ed., Humana Press, Totowa, N.J., 1993. Briefly, applying these factors, primer pairs are selected by position, similarity of melting temperature, internal stability, absence of internal homology or homology to each other, i.e., they won't stick to each other or to themselves, and the 3'-end will not form a stable hairpin loop back on itself.

Thus, in the present case, the goal is to have sets of primer pairs with approximately the same thermal profile, so that they can be effectively coamplified together. This goal can be achieved by having groups of primer pairs with approximately the same length and the same G/C content. In addition, it is preferred that the length of the gene region between the primer binding sites on a normal RB1 gene differ for each exon to be multiplexed as a group. Differences of only one base in length are sufficient, provided a high resolution gel capable of resolving one base differences is used in analyzing the amplification products. However, greater differences in length are preferred.

To evaluate compatibility of primers for use in coamplification, it is desirable to determine the predicted melting temperature for each primer. This can be accomplished in several ways. For example, the melting temperature, Tm can be calculated using either of the following equations:

$$Tm(° C.)=81.5+16.6\times\log [Na]+0.41\times(\% GC)-675/length$$

where [Na] is the concentration of sodium ions, and the % GC is in number percent, or $$Tm (° C.)=2\times(A+T)+4\times(G+C)$$

where A, T, G, and C represent the number of adenosine, thymidine, guanosine and cytosine residues in the primer. In general, primers for coamplification should be selected to have predicted melting temperatures differing by less than 4° C.

The process of selecting primers for use in the invention can be illustrated with reference to exons 4 and 6 of the RB1 gene. Two primer pairs have been identified for exon 4 and one primer pair has been identified for exon 6. Primer 4×5'–A is a 20-mer having the sequence ATATAGTAGT GATTTGATGT Seq. ID No: 122 which is homologous to a region in the intron immediately adjacent to the 5'-end of exon 4 of the RB1 gene. This region starts 122 bases from the 5'-end of the exon and extends to the base which is 103 bases from the exon. The primer has a predicted melting temperature of 50° C.

Primer 4×3'–A is a 20-mer having the sequence

ATGACATAAA AAATCAGAGT Seq. ID No: 123 which is homologous to a region in the intron adjacent to the 3'-end of exon 4 of the RB1 gene. This region starts 28 bases from the 3'-end of the exon and extends to the base which is 47 bases from the exon. This primer also has a melting temperature of 50° C.

Primer 6×5' is a 22-mer having the sequence

CACAAAAAGA AACACCCAAA AG Seq. ID No: 61 which is homologous to a region in the intron adjacent to the 5'-end of exon 6 of the RB1 gene. This region starts 72 bases from the 5'-end of the exon and extends to the base which is 93 bases from the exon. The primer has a predicted melting temperature of 62° C.

Primer 6×3' is a 22-mer having the sequence

TAATAAGCCA AGCAGAGAAT GA Seq. ID No: 26 which is homologous to a region of the intron adjacent to the 3'-end of exon 6 of the RB1 gene. This region starts 107 bases from the 3'-end of the exon and extends to the base which is 128 bases from the exon. The primer has a predicted melting temperature of 60° C.

These two primer pairs are effective for the amplification of exons 4 and 6 individually. They are not suited for use together in a multiplexed amplification, however, because the melting temperatures of the two pairs are too different. Furthermore, both of these primer pairs produce an amplification product which is 289 bases in length. Thus, the two primer pairs cannot be used with a common detectable label in a multiplexed reaction.

In order to amplify exon 4 and exon 6 in a single reaction, it is necessary to identify a different primer pair for one of the two exons which is compatible with the primer pair for the other exon. In this case, a suitable replacement is the primer pair identified by the inventors as 4×5'-B and 4×3'-B.

The primer 4×5'-B is a 22-mer having the sequence

AGTAGTGATT TGATGTAGAG CT Seq. ID No: 59 which is homologous to the region in the intron adjacent to the 5'-end of exon 4 that starts 98 bases from the 5'-end of the exon and extends to the base which is 119 bases from the exon. This primer has a melting temperature of 60° C. The primer 4×3'-B is a 22-mer having the sequence ATAAAAAATC AGAGTGTAAC CC Seq. ID No: 40 which is homologous to the region in the intron adjacent to the 3'-end of exon 4 starting 21 bases from the 5'-end of the exon and extends to the base which is 42 bases from the exon. This primer has a melting temperature of 58° C. Thus, these primers have melting temperatures which are much closer to the melting temperature of the exon 6 primers. Moreover, the amplification product has a length of 280 bases, which is 9 bases different from the amplification product of the exon 6 primers.

In addition to the selection of suitable primers, best results in the fragment length analysis are obtained if the amplification reaction is carried out for a limited number of amplification cycles. It will be understood, that the more cycles of amplification are carried out, the more of the desired product will be made and thus the easier its detection will be. It should also be recognized, however, that during the initial cycles (generally the first 20–25 cycles), the amount of DNA of the desired sequence doubles in each cycle, while thereafter the yield of desired product per cycle drops off. For maximum effectiveness in the method of the present invention, the amplification of the exons in the patient sample should be carried out only for a number of cycles during which doubling of DNA is still being achieved. Such amplification is referred to in the specification and claims hereof as "quantitative" amplification.

After amplification of the exons of RB1 gene, the amplification products are analyzed electrophoretically using a sequencing gel. Preferred gels will have a resolution of one base pair, so that one base deletions or insertions, which are relatively common in cases of retinoblastoma, can be identified. A suitable gel is a polyacrylamide gel of the type recommended for use with the Pharmacia A.L.F. Sequencer.

Figure 3:
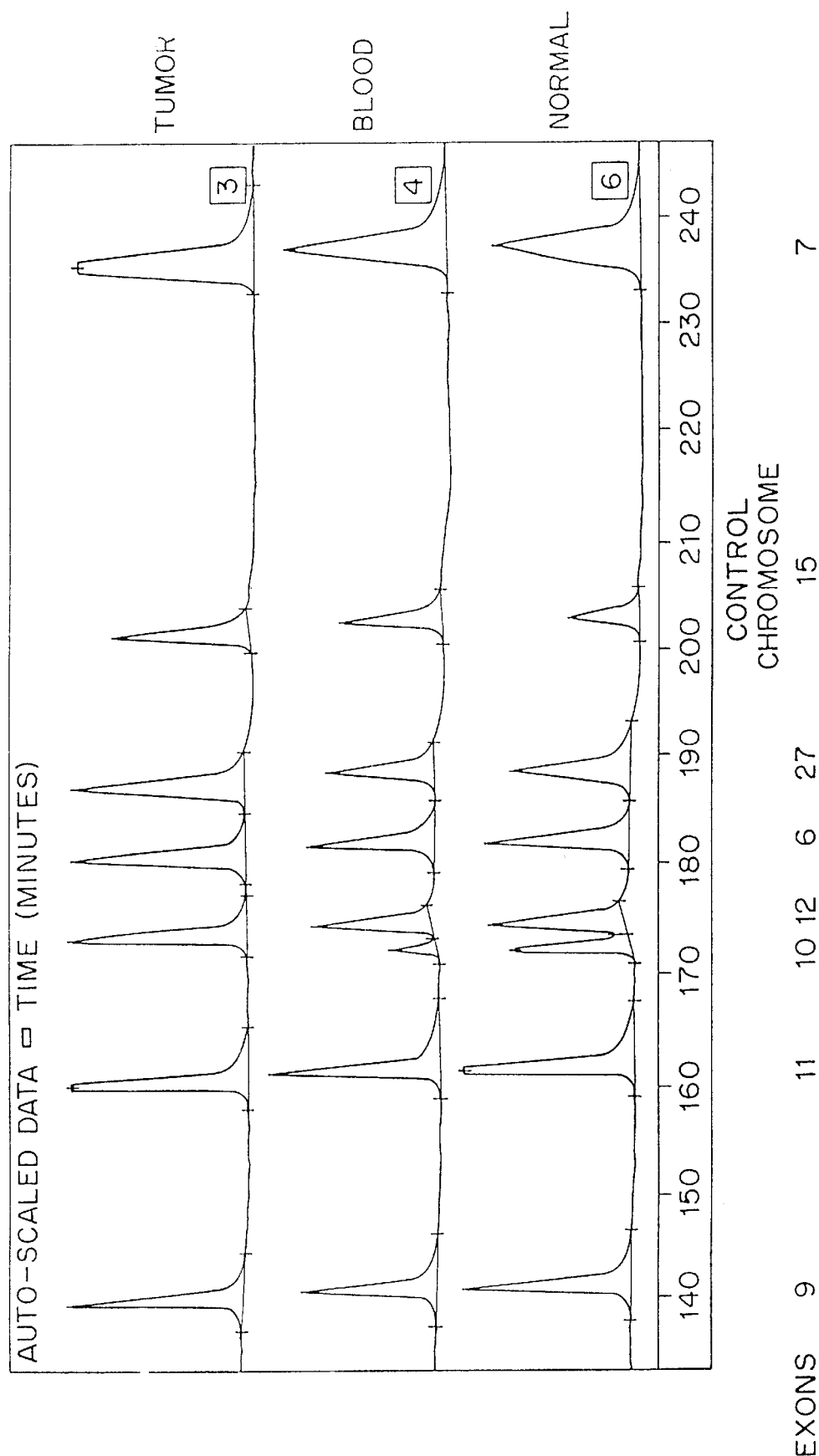
FIG. 3 shows a sample output of a Pharmacia A.L.F. Sequencer using fluorescein-labelled primers when exons 6, 9, 10, 11, 12 and 27 were coamplified.

The type of detector system used to analyze the gel depends on the type of label employed on the amplification primers. For example, in the case of radio-labeled primers, the gel might be analyzed by autoradiography. The preferred labels, however, are fluorophores which are detected using photodiodes, photomultipliers or other light sensitive devices. FIG. 3 shows a sample output of a Pharmacia A.L.F. Sequencer using fluorescein-labelled primers. Each peak in the output corresponds to a single-stranded fluorescein-labeled amplified DNA product from a PCR reaction migrating in the gel. Each exon of the RB1 gene and a control exon from a gene on chromosome 15 unrelated to RB1 migrate at a different rate. By comparison of the peaks from the patient samples to those of the wild type, it can be determined that a mutation exists, in this case the complete deletion of exon 10 from one allele, or the deletion of part of an exon and one of the priming sites. In a sample from the patient's tumor tissue, the mutation is homozygous (no exon 10), while in the blood of this patient, the exon 10 peak is reduced by 50% indicating that this patient carries the mutation in his or her somatic tissue, and therefore probably in their germline. The deletion of exon 10 leads to a severely truncated RB1 protein lacking many of the regions required for proper function, therefore it can be safely assumed that this is the disease causing mutation.

The second level of the hierarchy calls for the sequencing of one or more exons of the RB1 gene. Preferably, this sequencing process is performed on amplified DNA. The primers used in the pre-sequencing amplification can have the same sequence as those used in the first level of the test hierarchy, or they may be different. In either case, however, it is preferred that instead of the detectable labels used on the primers in the first level amplification, during pre-sequencing amplification one of the primers of each pair will be modified to facilitate recovery. For example, one primer of each pair may be biotinylated so that it can be recovered by binding to a streptavidin-coated support.

Once the mutation responsible for the retinoblastoma has been identified, additional tests are performed on family members to provide a basis for appropriate counseling and monitoring. Again, the most cost effective approach is hierarchical.

Figure 4:
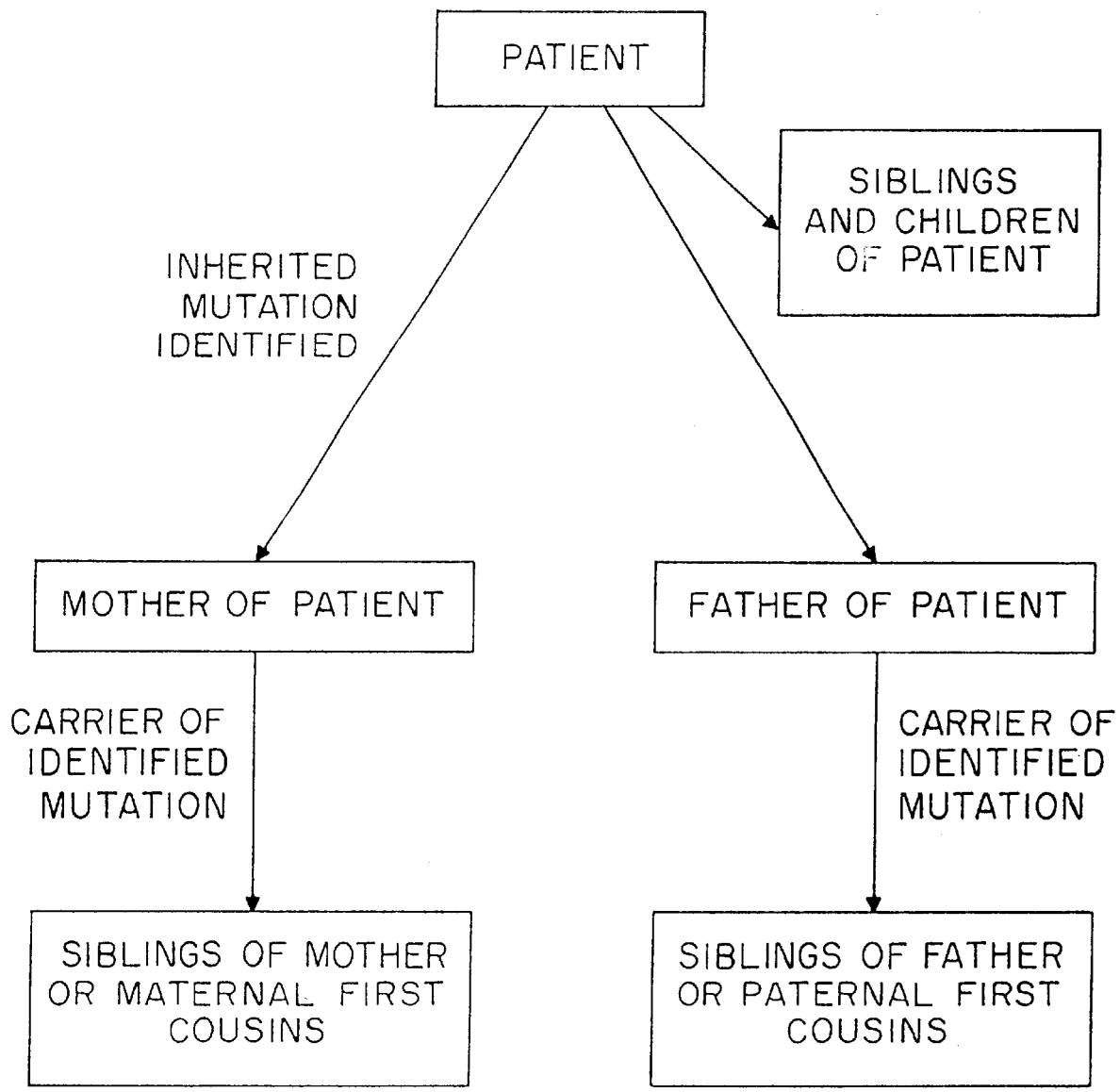
FIG. 4 shows a hierarchy for testing of family members of a patient after identification of the disease-associated mutation.

As shown in FIG. 4, an appropriate first step is the testing of the diagnosed child's parents and siblings. The test in this case involves amplification of the exon identified as having the disease-associated mutation using the level one primers. The amplified exon is then analyzed to determine if the same mutation is present. This may involve evaluation of the length and/or quantity of the amplification fragment, or sequencing, or both. If either parent is found to be a carrier of the disease-associated mutation, siblings of that parent should be tested to determine if they too carry the mutation. If they do, then their children should be tested. If they do not, then no testing of these first cousins of the diagnosed patient is necessary. If neither parent of the diagnosed patient is found to be a carrier of the disease-associated mutation, yet the mutation was detected in both blood and tumor tissue of the patient, then the mutation presumably arose through mosaicism, or during early development of the patient. In this case, all siblings of the patient should be tested, but other family members need not.

EXAMPLE 1

A blood sample is received from a patient diagnosed as suffering from retinoblastoma. Genomic DNA is prepared from the samples using a Qiagen QIAamp Kit according to the accompanying directions. Briefly, an aliquot of the sample, or a lymphocyte-containing fraction thereof, is combined with Proteinase K, mixed, and allowed to incubate to lyse the cells. Ethanol is added and the lysate is transferred to a QIAamp spin column from which DNA is recovered after several washings.

The genomic DNA is next amplified in five sets using multiplexing primers. Each 50 μl multiplexed PCR reaction contains 0.5 μg genomic DNA, 150 ng of each primer, 3.6 mM each dNTP, 42.5 μg Bovine Serum Albumin, 5 units Taq polymerase in a buffer containing 10% DMSO, 16 mM $(NH_4)_2SO_4$, 6.7 mM $MgCl_2$, 6.8 μM EDTA (pH 8.0) and 1 mM β-mercaptoethanol. The reaction mixture was initially incubated at 94° C. for 5 minutes and then subjected to an appropriate number of cycles of PCR in a Perkin-Elmer/Cetus thermocycler as follows:

denaturation 94° C., 30 seconds annealing 53° C. or 55° C., 30 seconds extension 72° C., 4 minutes—final extension 7 minutes.

In the first set, exons 2, 3, 5, 13 and 25 are amplified, together with a control sequence which is a DNA segment from chromosome 15, unrelated to RB1, for 18 cycles. The primers, one of each pair being labeled with fluorescein at the 5'-end, are

| exon | 5'-primer | 3'-primer |
|------|-----------|-----------|
| 2 | ACTGTGTGGT ATCCTTATTT TG [Seq. ID NO:1] | ATAGTGATTT GAAGTTGGTT TTA [Seq. ID NO:2] |
| 3 | ATACAGTTTT AACATAGTAT CCA [Seq. ID NO:3] | AAGTCTATTG AGAGGAAAAT [Seq. ID NO:4] |
| 5 | CTACTATGAC TTCTAAATTA CG [Seq. ID NO:5] | TCAAGATGTT TGAGATTATT CC [Seq. ID NO:6] |
| 13 | TGCTTATGTT CAGTAGTTGT G [Seq. ID NO:7] | TAATGGGGTG GGAGGTAGTT T [Seq. ID NO:8] |
| 25 | TCAAACTATA ACTTGAGGTT GC [Seq. ID NO:9] | AAAGAAATTG GTATAAGCCA GG [Seq. ID NO:10] |
| con | CTCACCCGCA CCTAAGTTT [Seq. ID NO:11] | CCAGGATGAG AGCGGATGGC A [Seq. ID NO:12] |

These primers result in amplified products with normal fragment lengths of 410, 262, 170, 461 and 316 base pairs, respectively. The control sequence produces a fragment having a length of 325 base pairs.

In the second set, exons 1, 8, 18, 21, 22, and 23 are amplified, together with the same control sequence, for 18 cycles. The primers, one of each pair of which is labeled with fluorescein, are

| exon | 5'-primer | 3'-primer |
|------|-----------|-----------|
| 1 | GCCCCAGTTC CCCACAGAC [Seq. ID NO:13] | ACCCCTCGCC CAAGAACCC [Seq. ID NO:14] |
| 8 | TCTAATGAAA CCTAATAAGT A [Seq. ID NO:15] | TGCTCATAAC AAAAGAAGTA A [Seq. ID NO:16] |
| 18 | TTTTTGTGTG TGGGAAGTAC A [Seq. ID NO:17] | ATTCTATTCC CTACAGTTTC TT [Seq. ID NO:18] |

-continued

| exon | 5'-primer | 3'-primer |
|---|---|---|
| 21 | GGCTAAAACA AAGAAAATGG [Seq. ID NO:19] | TTACCTATGT TATGTTATGG [Seq. ID NO:20] |
| 22 | TATGTGCTTC TTACCAGTCA AA [Seq. ID NO:21] | GGAGTCATTT TTGTTGGTGT TG [Seq. ID NO:22] |
| 23 | AATCTAATGT AATGGGTCCA CC [Seq. ID NO:23] | ATCAAAATAA TCCCCCTCTC AT [Seq. ID NO:24] |

These primers result in amplified products with normal fragment lengths of 591, 366, 418, 251, 496 and 283 base pairs, respectively.

In the third set, exons 6, 7, 9, 10, 11, 12 and 27 are amplified, together with the same control sequence, for 20 cycles. The primers, one of each pair being labeled with fluorescein, are These primers result in amplified products with normal fragment lengths of 228, 227, 343, 206, and 203 base pairs, respectively.

In the fifth set, exons 15 and 16 are amplified together, along with exons 17, 19, the RB1 promoter region and the same control sequence, for 20 cycles. The primers, one of each pair being labeled with fluorescein, are

| exon | 5'-primer | 3'-primer |
|---|---|---|
| 6 | AAAGAAACAC CCAAAAGATA [Seq. ID NO:25] | TAATAAGCCA AGCAGAGAAT GA [Seq. ID NO:26] |
| 7 | TTATGGATAT ACTCTACCCT GC [Seq. ID NO:27] | CCTCCATTTG TTGTATTTTG AC [Seq. ID NO:28] |
| 9 | TCAAGAGTCA AGAGATTAGA [Seq. ID NO:29] | ATTATCCTCC CTCCACAGTC TC [Seq. ID NO:30] |
| 10 | GTGCTGAGAG ATGTAATGA [Seq. ID NO:31] | TATCTAAAGC TCACTAAGC [Seq. ID NO:32] |
| 11 | TGAGACAACA GAAGCATTAT [Seq. ID NO:33] | TGAACAAATC TGAAACACTA T [Seq. ID NO:34] |
| 12 | CTCCCTTCAT TGCTTAACAC AT [Seq. ID NO:35] | AAAAGCAAGA AAAGATTATG G [Seq. ID NO:36] |
| 27 | ACTTACCCAG TACCATCAAT GC [Seq. ID NO:37] | TCAAGTGGCT TAGGAATCAC CC [Seq. ID NO:38] |

These primers result in amplified products with normal fragment lengths of 283, 423, 205, 264, 244, 270 and 297 base pairs, respectively.

In the fourth set, exons 4, 14, 20, 24 and 26 are amplified, together with the same control sequence, for 18 cycles. The primers, one of each pair being labeled with fluorescein, are

| exon | 5'-primer | 3'-primer |
|---|---|---|
| 4 | TTGAAAACGA AATAACAC [Seq. ID NO:39] | ATAAAAAATC AGAGTGTAAC CC [Seq. ID NO:40] |
| 14 | GTGATTTTCT AAAATAGCAG GC [Seq. ID NO:41] | CCAGGATGAT CTTGATGCC [Seq. ID NO:42] |
| 20 | GAAAAGAGTG GTAGAAAAGA GG [Seq. ID NO:43] | TAACAAGTAA GTAGGGAGGA GA [Seq. ID NO:46] |
| 24 | GTATTTATGC TCATCTCTGC [Seq. ID NO:45] | GTGTTTGAAT AACTGCATTT GG [Seq. ID NO:46] |
| 26 | CGAAAGCATC ATAGTTACTG G [Seq. ID NO:47] | ATATAACGAA AAGACTTCTT GC [Seq. ID NO:48] |

| exon | 5'-primer | 3'-primer |
|---|---|---|
| 15, 16 | CAATGCTGAC ACAAATAAGG TT [Seq. ID NO:49] | CCCCCGACCA AAGAAACACA [Seq. ID NO:50] |

-continued

| exon | 5'-primer | 3'-primer |
|---|---|---|
| 17 | ACCTTTCTAC TGTTTTCTTT GT [Seq. ID NO:51] | AAACACCTCT CACTAACAAT [Seq. ID NO:52] |
| 19 | TGTATAATCT GTGATTCTTA GC [Seq. ID NO:53] | GCAACATTAT CATTTCCATT TT [Seq. ID NO:54] |
| PROM | CCCACCAGAC TCTTTGTA [Seq. ID NO:55] | ACGTCCCCTG AGAAAAACCG GA [Seq. ID NO:56] |

These primers result in amplified products with normal fragment lengths of 335, 371, 363, and 316 base pairs, respectively.

After amplification, the products from each amplification reaction are denatured and loaded onto a polyacrylamide sequencing gel in a Pharmacia A.L.F. automated sequencer. The single-stranded amplification products migrate through the gel at a rate determined by their length, and are detected using the fluorescence of the fluorescein label which was attached to the primers.

EXAMPLE 2

Genomic DNA prepared as in Example 1 is amplified in six sets using multiplexing primers. Each 25 µl multiplexed PCR reaction contains 0.3 µg genomic DNA, 0.2 mM each dNTP, 1.5 mM MgCl$_2$, 2.5 U (0.5 µl of 5U/µl) Taq polymerase (Perkin-Elmer, Foster City, Calif.)in a buffer of 1X Perkin-Elmer PCR Buffer II, or 10 mM Tris-HCl pH 8.3, 50 mM KCl, and 0.001% (w/v) gelatin. The reaction mixture is initially incubated at 94° C. for 1 minute in a Perkin Elmer 9600 thermocycler, or for 2 minutes in a Robocycler in Gradient Mode. Subsequent cycles depend on the multiplexing group and the thermocycler equipment being utilized.

The first group of primers amplifies exons 4, 5, 7, 8, 10, 11, 19 and 25 of the RB1 gene using the same primers as in Example 1. This first group also contains primers to amplify the same control sequence used in Example 1. The primers are combined in a stock mixture. 1.3 µl of the stock mixture is used in each 25 µl reaction mixture to provide 100 ng of each of the primers for the control sequence and exon 19, and 50 ng of each of the primers for the other exons. The amplification is performed in a Perkin-Elmer 9600 thermocycler for 19 cycles as follows:

| denaturation | 94° C., 30 seconds |
| annealing | 52° C., 30 seconds |
| extension | 65° C., 2 minutes - final extension 2 minutes, | or in a Robocyler Gradient Mode Thermocycler for 19 cycles as follows:

| denaturation | 94° C., 1 minute 30 seconds |
| annealing | 52° C., 1 minute 30 seconds |
| extension | 65° C., 4 minutes - final extension 7 minutes. |

The second group of primers amplifies exons 12, 15/16, 17, 18 and 21 of the RB1 gene using the same primers as in Example 1. This second group also contains primers to amplify the same control sequence used in Example 1. The primers are combined in a stock mixture. 1.3 µl of the stock mixture is used in each 25 µl reaction mixture to provide 100 ng of each of the primers for the control sequence and exons 12 and 18, and 50 ng of each of the primers for the other exons. The amplification is performed in a Perkin-Elmer 9600 thermocycler for 19 cycles as follows:

| denaturation | 94° C., 1 minute 30 seconds |
| annealing | 52° C., 1 minute 30 seconds |
| extension | 65° C., 4 minutes - final extension 7 minutes. | or in a Robocyler Gradient Mode Thermocycler for 19 cycles as follows:

| denaturation | 94° C., 1 minute 30 seconds |
| annealing | 52° C., 1 minute 30 seconds |
| extension | 65° C., 4 minutes - final extension 7 minutes. |

The third group of primers amplifies exons 3, 9, 13, 20, 23, and 24 of the RB1 gene using the same primers as in Example 1. This third group also contains primers to amplify a portion of chromosome 15 as a control sequence. In this case, however, the primers are selected to provide a shorter fragment length of 282 nt to avoid possible ambiguity with the exon 20 fragment. The sequence of these primers is as follows:

5' primer:

GCCCCTCACC CGCACCTAAGT   Seq. ID No: 124

3' primer:

GCCGTCCCTC CAAGCACTG   Seq. ID No: 125

The primers are combined in a stock mixture. 1.0 µl of the stock mixture is used in each 25 µl reaction mixture to provide 100 ng of each of the primers for exons 3 and 20, 25 ng of each primer for the control sequence and exon 9, and 50 ng of each of the primers for the other exons. The amplification is performed in a Perkin-Elmer 9600 thermocycler for 19 cycles as follows:

| denaturation | 94° C., 30 seconds |
| annealing | 52° C., 30 seconds |
| extension | 65° C., 2 minutes - final extension 2 minutes, | or in a Robocyler Gradient Mode Thermocycler for 19 cycles as follows:

| denaturation | 94° C., 1 minute 30 seconds |
| annealing | 54° C., 1 minute 30 seconds |
| extension | 65° C., 4 minutes - final extension 7 minutes. |

The fourth group of primers amplifies exons 2, 6, 14, 22, 26 and 27 of the RB1 gene using the same primers as in Example 1. This fourth group also contains primers to amplify the same control sequence used with the third group. The primers are combined in a stock mixture. 1.4 µl of the stock mixture is used in each 25 µl reaction mixture to provide 100 ng of each of the primers for the control sequence and exons 2, 22 and 27, and 50 ng of each of the primers for the other exons. The amplification is performed in a Perkin-Elmer 9600 thermocycler for 19 cycles as follows:

| denaturation | 94° C., 30 seconds |
|---|---|
| annealing | 58° C., 30 seconds |
| extension | 65° C., 2 minutes - final extension 2 minutes, | or in a Robocycler Gradient Mode Thermocycler for 19 cycles as follows:

| denaturation | 94° C., 1 minute 30 seconds |
|---|---|
| annealing | 58° C., 1 minute 30 seconds |
| extension | 65° C., 4 minutes - final extension 7 minutes. |

Finally, the promoter region and exon 1 are each amplified separately as fifth and sixth amplification "groups." These fifth and sixth amplification groups contain primers to amplify the same control sequence used with the first set. The primers are combined in a stock mixture with a buffer which is the same as that described above, with the addition of 10% DMSO (volume per volume). 1.4 ul of the stock mixture is used in each 25 ul reaction mixture to provide 100 ng of each of the primers for the control sequence and exon 1 or the promoter, respectively. The amplification starts by annealing the primers with the genomic DNA after first heating the reaction mixture to 94 degrees for 2 minutes. The amplification is performed in a Perkin-Elmer 9600 thermocycler for 19 cycles as follows: denaturation 94 degrees, 60 secs.

annealing 61 degrees, 90 secs extension 72 degrees secs, with a final extension for 4 minutes at 72 degrees.

EXAMPLE 3

FIG. 3 shows the peaks detected in the third amplification group (exons 6, 9, 10, 11, 12 and 27 and the control exon) when samples of a diagnosed individualls blood and tumor material were treated as described in Example 1 and compared to a normal sample. The peak associated with exon 10 is completely missing in the tumor sample, and is present at only half intensity in the blood sample.

EXAMPLE 4

Blood samples were obtained from a juvenile female patient diagnosed with bilateral retinoblastoma, the patient's brother, biological parents, two maternal aunts and both maternal grandparents. The samples were evaluated in accordance with the procedure outlined in Example 1. Based on this test, the patient was found to be homozygous for a one-base pair deletion in exon 19 of the RB1 gene. The patient's mother was found to be heterozygous for the same mutation. No other family member tested had any detected abnormality in the RB1 gene.

Exon 19 from the patient was subsequently sequenced to confirm the presence of a mutation which would lead to retinoblastoma. Sequencing was performed by selectively amplifying exon 19 using the following primers:

5'-primer

| ATGACAAGCA GTTTTCCTAT TA | Seq. ID No: 89 |
|---|---|

3'-primer

| GCAACATTAT CATTTCCATT TT | Seq. ID No: 90 |
|---|---|

The 5'-primer was biotinylated to permit recovery of one strand of the amplified DNA for sequencing using streptavidin coated magnetic beads.

The amplification was performed in a Perkin-Elmer/Cetus thermocycler, and each amplification cycle was as follows:

| denaturing | 96° C., 30 seconds |
|---|---|
| annealing | 55° C., 30 seconds |
| extending | 71° C., 50 seconds |

A total of 40 amplification cycles were used.

The amplified product was then sequenced using an AutoRead™ Sequencing Kit by mixing it with a fluorescent nested primer having the sequence

| GATGAGGAAA CTGAGACA | Seq. ID No: 103 |
|---|---| and annealing buffers supplied with the kit, and then sequentially adding extension buffer, and DNA polymerase. The sample was then divided into four portion, and one of the four nucleotide "mixes" from the kit was added to each portion. The portions were then loaded onto individual lanes of a sequencing gel and analyzed with a Pharmacia A.L.F. Sequencer. The results of the sequencing showed that the one base pair deletion results in a premature stop codon, and thus explained the occurrence of the retinoblastoma.

Based on these results, pre-natal testing was suggested in any future pregnancies of either the patient or her parents. No testing or monitoring is necessary for other family members, however, since they did not carry the mutation.

EXAMPLE 5

Amplification primers for use prior to sequencing have been developed for each exon (except exons 15 and 16 which share a common set of primers) and the promoter region of the RB1 gene. These primers are listed in Table 1, together with appropriate amplification parameters. In some cases, the primers are the same as those used in the fragment length/quantity analysis. In other cases, the preferred amplification primers are different. It will be understood, however, that primers of either type can be used for both purposes.

TABLE 1

PCR PRIMERS FOR AMPLIFICATION OF RB1 EXONS

| exon | 5'-primer | 3'-primer | initial denature temp (° C.) time (sec) | Denature temp (° C.) time (sec) | Anneal temp (° C.) time (sec) | Extend temp (° C.) time (sec) | cycles | final ext temp (° C.) time (sec) |
|---|---|---|---|---|---|---|---|---|
| 1 | GCCCCAGTTC CCCACAGACG C [Seq. ID NO:57] | ACCCTTCGCC CAAGAACCCA [Seq. ID NO:14] | 96 180 | 96 50 | 63 50 | 72 60 | 30 | 72 180 |
| 2 | ACTGTGTGGT ATCCTTATTT TG [Seq. ID NO:1] | TCCTCTGGGT AATGGAATTA TT [Seq. ID NO:58] | 96 180 | 94 50 | 58 50 | 71 60 | 40 | 71 180 |
| 3 | ATAQAGTTTT AACATAGTAT CCA [Seq. ID NO:3] | AAGTCTATTG AGAGGAAAAT CC [Seq. ID NO:4] | 96 180 | 96 30 | 55 30 | 71 50 | 40 | 71 180 |
| 4 | AGTAGTGATT TGATGTAGAG CT [Seq. ID NO:59] | ATAAAAAATC AGAGTGTAAC CC [Seq. ID NO:40] | 96 180 | 96 30 | 55 30 | 71 50 | 40 | 71 180 |
| 5 | CTACTATGAC TTCTAAATTA CG [Seq. ID NO:5] | ATCAAGATGT TTGAGATTAT TCC [Seq. ID NO:60] | 96 180 | 96 30 | 55 30 | 71 50 | 40 | 71 180 |
| 6 | CACAAAAAGA AACACCCAAA AG [Seq. ID NO:61] | TAATAAGCCA AGCAGAGAAT GA [Seq. ID NO:26] | 96 180 | 94 50 | 58 50 | 71 60 | 40 | 71 180 |
| 7 | TACTCTACCC TGCGATTTTC TC [Seq. ID NO:62] | CTCCATTTG TTGTATTTTG AC [Seq. ID NO:28] | 96 180 | 94 50 | 58 50 | 71 60 | 40 | 71 180 |
| 8 | TCTAATGAAA CCTAATAAGT A [Seq. ID NO:15] | TGCTCATAAC AAAAGAAGTA A [Seq. ID NO:16] | 94 180 | 94 60 | 50 60 | 71 60 | 30 | 71 180 |
| 9 | ATGGGGGATT GACACCTCTA AC [Seq. ID NO:63] | ATTATCCTCC CTCCACAGTC TC [Seq. ID NO:30] | 96 300 | 94 50 | 61 50 | 71 60 | 40 | 71 180 |
| 10 | TAATGAAATC TGTGCCTCTG [Seq. ID NO:64] | TATCTAAAGG TCACTAAGC [Seq. ID NO:32] | 96 180 | 96 30 | 52 30 | 71 50 | 40 | 71 180 |
| 11 | TATGATTTTA TGAGACAACA GA [Seq. ID NO:65] | TGAACAAATC TGAAACACTA T [Seq. ID NO:34] | 94 300 | 94 30 | 51 30 | 71 50 | 40 | 71 180 |
| 12 | AACTTGGGAG ATTGAAAACA T [Seq. ID NO:66] | AAAAGCAAGA AAAGATTATG G [Seq. ID NO:36] | 94 300 | 94 30 | 51 30 | 71 50 | 40 | 71 180 |
| 13 | TGCTTATGTT CAGTAGTTGT G [Seq. ID NO:7] | TAATGGGGTG GGAGGTAGTT T [Seq. ID NO:8] | 96 180 | 96 30 | 55 30 | 71 50 | 40 | 71 180 |
| 14 | AAAGCAGGAG GATCTCTTGA GC [Seq. ID NO:67] | CCAGGATGAT CTTGATGCC [Seq. ID NO:42] | 96 300 | 94 50 | 57 50 | 71 60 | 40 | 71 180 |
| 15, 16 | CAATGCTGAC ACAAATAAGG TT [Seq. ID NO:49] | CTCCCCCGAC CACCGAAACA C [Seq. ID NO:68] | 96 180 | 94 50 | 58 50 | 71 60 | 40 | 71 180 |
| 17 | ACCTTTCTAC TGTTTTCTTT GT [Seq. ID NO:51] | ATTAGATGGT TTAGGGTGCT C [Seq. ID NO:69] | 96 180 | 96 30 | 55 30 | 71 50 | 40 | 71 180 |
| 18 | TTTTTGTGTG TGGGAAGTA [Seq. ID NO:70] | ATTCTATTCC CTACAGTTTC TT [Seq. ID NO:18] | 96 300 | 96 50 | 53 30 | 71 60 | 40 | 71 180 |
| 19 | ATGACAAGCA GTTTTCCTAT T [Seq. ID NO:71] | GCAACATTAT CATTTCCATT TT [Seq. ID NO:54] | 96 180 | 96 30 | 55 30 | 71 50 | 40 | 71 180 |
| 20 | GAAAAGAGTG GTAGAAAAGA GG [Seq. ID NO:43] | TAACAAGTAA GTAGGGAGGA GA [Seq. ID NO:44] | 96 180 | 94 50 | 53 50 | 71 60 | 40 | 71 180 |
| 21 | GGCTAAAAGA AAGAAAATGG [Seq. ID NO:19] | TTACCTATGT TATGTTATGG [Seq. ID NO:20] | 94 300 | 94 30 | 51 30 | 71 50 | 40 | 71 180 |
| 22 | TATGTGCTTC TTACCAGTCA AA [Seq. ID NO:21] | GGAGTCATTT TTGTTGGTGT TG [Seq. ID NO:22] | 96 180 | 94 50 | 58 50 | 71 60 | 40 | 71 180 |
| 23 | CCAGGGTAGG TCAAAAGTAT CC [Seq. ID NO:72] | ATCAAAATAA TCCCCCTCTC AT [Seq. ID NO:24] | 96 180 | 94 50 | 58 50 | 71 60 | 40 | 71 180 |
| 24 | ATGTATTTAT GCTCATCTCT GC [Seq. ID NO:73] | GTGTTTGAAT AACTGCATTT GG [Seq. ID NO:46] | 96 180 | 94 50 | 58 50 | 71 60 | 40 | 71 180 |
| 25 | TCAAACTATA ACTTGAGGTT GC [Seq. ID NO:9] | AAAGAAATTG GTATAAGCCA GG [Seq. ID NO:10] | 96 180 | 94 50 | 58 50 | 71 60 | 40 | 71 180 |
| 26 | TCGAAAGCAT CARAGTTACT GG [Seq. ID NO:74] | ATATAACGAA AAGACTTCTT GC [Seq. ID NO:48] | 96 180 | 96 30 | 55 30 | 71 50 | 40 | 71 180 |
| 27 | ACTTACCCAG TACCATCAAT GC [Seq. ID NO:37] | TCAAGTGGCT TAGGAATCA CC [Seq. ID NO:38] | 96 180 | 94 50 | 58 50 | 71 60 | 40 | 71 180 |
| prom | ACAGTCACCC ACCAGACTCT TT [Seq. ID NO:75] | ACGTCCCCTG AGAAAAACCG GA [Seq. ID NO:56] | 96 240 | 96 50 | 64 50 | 71 60 | 30 | 72 180 |

EXAMPLE 6

In determining the sequences of exons in the method of the invention, the primers identified above as useful as amplification primers can be used as the sequencing primer. Sequencing primers have been developed for each exon, however, which are nested inside the amplification primers listed in Table 1, i.e., closer to the exon. Table 2 lists these sequencing primers. These sequencing primers could also be used, and in fact in some cases are used, in the fragment analysis as described in Example 1.

TABLE 2

SEQUENCING PRIMERS

| EXON | 3'Sequencing Primer | 5'Sequencing Primer |
|------|---------------------|---------------------|
| 1 | CGCCCGCCCT ACGCACACC [Seq. ID NO:76] | CGTGAGCGCG GGCGGAA [Seq. ID NO:77] |
| 2 | TAGTGATTTG AAGTTGTT [Seq. ID NO:78] | ATGTGCAAAC TATTGAAA [Seq. ID NO:79] |
| 3 | CTATTGAGAG GAAAATCCAG AA [Seq. ID NO:80] | TAACATAGTA GTATCCAGTG T [Seq. ID NO:81] |
| 4 | ATCAGAGTGA AACCCTAA [Seq. ID NO:82] | TTGAAAACGA AATAACAC [Seq. ID NO:39] |
| 5 | AGATGTTTGA GATTATTCCA [Seq. ID NO:83] | TAAATTACGA AAAAATGTTA [Seq. ID NO:84] |
| 6 | CAGAGAATGA GGGAGGAGTA [Seq. ID NO:85] | AAAGAAACAC CCAAAAGATA [Seq. ID NO:25] |
| 7 | TGTCTTATCT TTCCTTCTAT [Seq. ID NO:86] | TGCGATTTTC TCTCATACAA [Seq. ID NO:87] |
| 8 | CATAACAAAA GAAGTAAAT [Seq. ID NO:88] | ATGTTACCAA GATTATTTT [Seq. ID NO:89] |
| 9 | TCCACAGTCT CAAAACATTA [Seq. ID NO:90] | TCAAGACTCA AGAGATTAGA [Seq. ID NO:29] |
| 10 | TATCTAMGC AAATCAATC [Seq. ID NO:91] | GTGCTGAGAG ATGTAATGA [Seq. ID NO:31] |
| 11 | AATCTGAAAC ACTATAAA [Seq. ID NO:92] | TGAGACAACA GAAGCATTAT [Seq. ID NO:33] |
| 12 | TGTTAGATAG GAGATTAGT [Seq. ID NO:93] | CCCTTCATTG CTTAACAC [Seq. ID NO:94] |
| 13 | TCTGATTAGA CAGTATCC [Seq. ID NO:95] | GAACTGGAAA GATGCTGC [Seq. ID NO:96] |
| 14 | TCTTGATGCC TTGACCTC [Seq. ID NO:97] | GTGATTTTCT AAAATAGCAG GC [Seq. ID NO:41] |
| 15,16 | ATACTTACTT CTATAAAAAG [Seq. ID NO:98] | CCAAAGAAAC ACACCACATT [Seq. ID NO:99] |
| 17 | AAACACCTCT CACTAACAAT [Seq. ID NO:52] | CTGATAATAA CTTCCAAAAA [Seq. ID NO:100] |
| 18 | TCCCTACAGT TTCTTTAT [Seq. ID NO:101] | TTTGATATGT ACCTGGGA [Seq. ID NO:102] |
| 19 | GATGAGGAAA CTGAGACA [Seq. ID NO:103] | GTGATTCTTA GCCAACTT [Seq. ID NO:104] |
| 20 | AGTAGGGAGG AGAGAAGGTG [Seq. ID NO:105] | CAAAATGAAC AGTAAAAATG [Seq. ID NO:106] |
| 21 | CTATGTTATG TTATGGAT [Seq. ID NO:107] | AAAGAAAGAA AATGGTAT [Seq. ID NO:108] |
| 22 | TGGTGGACCC ATTACATT [Seq. ID NO:109] | ACCAGTCAAA AAGTATTA [Seq. ID NO:110] |
| 23 | TCTCATTCTT TACTACTT [Seq. ID NO:111] | TTGGAAAAAT CTAATGTA [Seq. ID NO:112] |
| 24 | CTTTTATACT TACAATGC [Seq. ID NO:113] | TATGGTTTTT TATTACTA [Seq. ID NO:114] |
| 25 | ATGACCATCT CAGCTACT [Seq. ID NO:115] | TTGCTAACTA TGAAACACT [Seq. ID NO:116] |
| 26 | ATTTGTTTATT TCGTTTAC [Seq. ID NO:117] | ATTTGAGTTT TCCATTTA [Seq. ID NO:118] |
| 27 | CTTAGGAATC ACCCAAACA [Seq. ID NO:119] | AGTACCATCA ATGCTGTTA [Seq. ID NO:120] |
| prom | CTGAGAAAA CCGGACGCG [Seq. ID NO:121] | CCCACCAGAC TCTTTGTA [Seq. ID NO:55] |

The primers used in the present invention are advantageously packaged as kits for the detection of mutations in the RB1 gene. Such a kit may contain a single pair of primers, useful for quantitative amplification of a single exon, or multiple pairs of primers useful for amplification of multiple exons. Such kits may further include amplification and/or sequencing primers for one or more exons. Such kits may also include reagents other than primers for use in the amplification reaction, such a polymerase and buffers, but this is optional.

Preferred kits in accordance with the invention comprise a plurality of primer pairs useful in the coamplification of a plurality of exons of the RB1 gene. Primer pairs in such kits are selected to have a common melting temperature and to produce amplification products having differing lengths.

---

What is claimed is:

1. A method for identifying mutations in a sample retinoblastoma gene comprising the steps of:

(a) quantitatively coamplifying a plurality of exons of the sample retinoblastoma gene using primers complementary to intron regions immediately flanking each of the plurality of exons;

(b) determining the lengths of the amplification products for each amplified sample exon and comparing that length to the length of amplification products obtained when a wild-type retinoblastoma gene is amplified using the same primers, whereby differences in length between an amplified sample exon and the corresponding amplified wild-type exon reflect the occurrence on an insertion or deletion mutation in the sample retinoblastoma gene; and (c) determining the nucleic acid sequence of each exon identified in step (b) to contain an insertion or deletion mutation, or in the event no insertion or deletion mutations are identified, determining the nucleic acid sequence of at least one exon of the retinoblastoma gene, sufficient exons being sequenced to identify the presence of a mutation if one exists in the sample retinoblastoma gene, wherein in step (a) exons 4, 5, 7, 8, 10, 11, 19 and 25 are coamplified in a single reaction.

2. A method for genetic screening of family members of an individual diagnosed as having retinoblastoma, comprising the steps of:

(a) obtaining a patient blood sample from the diagnosed individual;

(b) quantitatively amplifying at least one exon of the retinoblastoma gene in cells from the patient blood sample using primers complementary to intron regions immediately flanking each exon amplified;

(c) determining the length of the amplification product for each exon amplified and comparing that length to the length of amplification products obtained when a wild-type retinoblastoma gene is amplified using the same primers, whereby differences in length between an amplified sample exon and the corresponding amplified wild-type exon reflect the occurrence of an inherited insertion or deletion mutation in the retinoblastoma gene of the diagnosed individual; and (d) if an inerited mutation is identified, obtaining blood samples from the biological parents of the diagnosed individual; quantitatively amplifying the exon of the retinoblastoma gene found to contain an insertion or deletion mutation in the patient blood sample in cells from the parent blood samples using the same primers used to amplify the exons in the patient blood sample; and determining the length of the amplification product for the exon in the amplified parent blood samples and comparing that length to the length of amplification products obtained when the patient blood sample was amplified, wherein in step (b) exons 4, 5, 7, 8, 10, 11, 19 and 25 are coamplified in a single reaction.

3. A method for generating a report on the nature of a mutation causing retinoblastoma in a patient, comprising the steps of (a) obtaining a sample of patient tissue containing a sample retinoblastoma gene, (b) quantitatively coamplifying a plurality of exons of the sample retinoblastoma gene using primers complementary to intron regions flanking each amplified exon;

(c) determining the lengths of the amplification products for each amplified sample exon and comparing that length to the length of amplification products obtained when a wild-type retinoblastoma gene is amplified using the same primers, whereby differences in length between an amplified sample exon and the corresponding amplified wild-type exon reflect the occurrence on an insertion or deletion mutation in the sample retinoblastoma gene;

(d) determining the nucleic acid sequence of each exon identified in step (c) to contain an insertion or deletion mutation, or in the event no insertion or deletion mutations are identified, the nucleic acid sequence of at least one exon of the sample retinoblastoma gene, sufficient exons being sequenced to identify the presence of a mutation if one exists in the sample retinoblastoma gene; and (e) generating a report identifying the exon in which the mutation, if any, is located, wherein in step (b) exons 4, 5, 7, 8, 10, 11, 19 and 25 are coamplified in a single reaction.

4. A method according to claim 1, further comprising coamplifying exons 12, 15, 16, 17, 18 and 21 in a single reaction mixture.

5. A method according to claim 1, further comprising coamplifying exons 3, 9, 13, 20, 23 and 24 in a single reaction mixture.

6. A method according to claim 1, further comprising coamplifying exons 2, 6, 14, 22, 26 and 27 in a single reaction mixture.

7. A method according to claim 2, wherein if at least one parent is found to carry the mutation found in the patient, further performing the steps of obtaining aunt/uncle blood samples from the siblings of the parent found to carry the mutation;

quantitatively amplifying the exon of the RB 1 gene found to contain an insertion or deletion mutation in the patient blood sample in cells from the aunt/uncle blood samples using the same primers used to amplify the exons in the patient blood sample; and determining the length of the amplification product for the exon in the amplified aunt/uncle blood samples and comparing that length to the length of amplification products obtained when the patient blood sample was amplified.

8. A kit for identification of mutations in the retinoblastoma gene, comprising a plurality of primer pairs for multiplex coamplification of a selected plurality of exons of the retinoblastoma gene, wherein one member of each primer pair is labeled with a detectable label, and wherein the primer pairs are selected to have a common melting temperature and to produce amplification products having differing lengths and wherein the primers pairs bind to intron regions immediately flanking each of the selected plurality of exons, said kit comprising at least one set of primers for amplification of the selected plurality of exons of the retinoblastoma gene selected from among the following primer pairs:

(a) GCCCCAGTTC CCCACAGAC     Seq. ID No: 13
and
ACCCCTCGCC CAAGAACCCA     Seq. ID No: 14;

(b) ACTGTGTGGT ATCCTTATTT TG     Seq. ID No: 1
and
ATAGTGATTT GAAGTTGGTT TTA     Seq. ID No: 2;

(c) ATACAGTTTT AACATAGTAT CCA     Seq. ID No: 3
and
AAGTCTATTG AGAGGAAAAT CC     Seq. ID No: 4;

(d) TTGAAAACGA AATAACAC     Seq. ID No: 39
and
ATAAAAAATC AGAGTGTAAC CC     Seq. ID No: 40;

(e) CTACTATGAC TTCTAAATTA CG     Seq. ID No: 5
and
TCAAGATGTT TGAGATTATT CC     Seq. ID No: 6;

(f) AAAGAAACAC CCAAAAGATA     Seq. ID No: 25
and
TAATAAGCCA AGCAGAGAAT GA     Seq. ID No: 26;

(g) TTATGGATAT ACTCTACCCT GC     Seq. ID No: 27
and
CCTCCATTTG TTGTATTTTG AC     Seq. ID No: 28;

(h) TCTAATGAAA CCTAATAAGT A     Seq. ID No: 15

-continued

|   |   |   |
|---|---|---|
| and | | |
| TGCTCATAAC AAAAGAAGTA A | Seq. ID No: 16; | |
| (i) TCAAGAGTCA AGAGATTAGA | Seq. ID No: 29 | |
| and | | |
| ATTATCCTCC CTCCACAGTC TC | Seq. ID No: 30; | |
| (j) GTGCTGAGAG ATGTAATGA | Seq. ID No: 31 | |
| and | | |
| TATCTAAAGG TCACTAAGC | Seq. ID No: 32; | |
| (k) TGAGACAACA GAAGCATTAT | Seq. ID No: 33 | |
| and | | |
| TGAACAAATC TGAAACACTAT | Seq. ID No: 34; | |
| (l) CTCCCTTCAT TGCTTAACAC AT | Seq. ID No: 35 | |
| and | | |
| AAAAGCAAGA AAAGATTATG G | Seq. ID No: 36; | |
| (m) TGCTTATGTT CAGTAGTTGT G | Seq. ID No: 7 | |
| and | | |
| TAATGGGGTG GGAGGTAGTT T | Seq. ID No: 8; | |
| (n) GTGATTTTCT AAAATAGCAG GC | Seq. ID No: 41 | |
| and | | |
| CCAGGATGAT CTTGATGCC | Seq. ID No: 42; | |
| (o) CAATGCTGAC ACAAATAAGG TT | Seq. ID No: 49 | |
| and | | |
| CCCCCGACCA AAGAAACACA | Seq. ID No: 50; | |
| (p) ACCTTTCTAC TGTTTTCTTT GT | Seq. ID No: 51 | |
| and | | |
| AAACACCTCT CACTAACAAT | Seq. ID No: 52; | |
| (q) TTTTTGTGTG TGGGAAGTAC A | Seq. ID No: 17 | |
| and | | |
| ATTCTATTCC CTACAGTTTC TT | Seq. ID No: 18; | |
| (r) TGTATAATCT GTGATTCTTA GC | Seq. ID No: 53 | |
| and | | |
| GCAACATTAT CATTTCCATT TT | Seq. ID No: 54; | |
| (s) GAAAAGAGTG GTAGAAAAGA GG | Seq. ID No: 43 | |
| and | | |
| TAACAAGTAA GTAGGGAGGA GA | Seq. ID No: 44; | |
| (t) GGCTAAAAGA AAGAAAATGG | Seq. ID No: 19 | |
| and | | |
| TTACCTATGT TATGTTATGG | Seq. ID No: 20; | |
| (u) TATGTGCTTC TTACCAGTCA AA | Seq. ID No: 21 | |
| and | | |
| GGAGTCATTT TTGTTGGTGT TG | Seq. ID No: 22; | |
| (v) AATCTAATGT AATGGGTCCA CC | Seq. ID No: 23 | |
| and | | |
| ATCAAAATAA TCCCCCTCTC AT | Seq. ID No: 24; | |
| (w) GTATTTATGC TCATCTCTGC | Seq. ID No: 45 | |
| and | | |
| GTGTTTGAAT AACTGCATTT GG | Seq. ID No: 46; | |
| (x) TCAAACTATA ACTTGAGGTT GC | Seq. ID No: 9 | |
| and | | |
| AAAGAAATTG GTATAAGCCA GG | Seq. ID No: 10; | |
| (y) CGAAAGCATC ATAGTTACTG G | Seq. ID No: 47 | |
| and | | |
| ATATAACGAA AAGACTTCTT GC | Seq. ID No: 48; and | |
| (z) ACTTACCCAG TACCATCAAT GC | Seq. ID No: 37 | |
| and | | |
| TCAAGTGGCT TAGGAATCAC CC | Seq. ID No: 38. | |

9. A kit for identification of mutations in the retinoblastoma gene, comprising a plurality of primer pairs for multiplex coamplification of a selected plurality of exons of the retinoblastoma gene, wherein one member of each primer pair is labeled with a detectable label, and wherein the primer pairs are selected to have a common melting temperature and to produce amplification products having differing lengths and wherein the primers pairs bind to intron regions immediately flanking each of the selected plurality of exons, said kit comprising primers selected to permit coamplification of exons 2, 3, 5, 13 and 25 of the retinoblastoma gene.

10. A kit according to claim 9, comprising the following coamplification primers:

| exon | 5'-primer | 3'-primer |
|---|---|---|
| 2 | Seq ID No:1 | Seq ID No:2 |
| 3 | Seq ID No:3 | Seq ID No:4 |
| 5 | Seq ID No:5 | Seq ID No:6 |
| 13 | Seq ID No:7 | Seq ID No:8 |
| 25 | Seq ID No:9 | Seq ID No:10. |

11. A kit for identification of mutations in the retinoblastoma gene, comprising a plurality of primer pairs for multiplex coamplification of a selected plurality of exons of the retinoblastoma gene, wherein one member of each primer pair is labeled with a detectable label, and wherein the primer pairs are selected to have a common melting temperature and to produce amplification products having differing lengths and wherein the primers pairs bind to intron regions immediately flanking each of the selected plurality of exons, said kit comprising primers selected to permit coamplification of exons 1, 8, 18, 21, 22, and 23 of the retinoblastoma gene.

12. A kit according to claim 11, comprising the following coamplification primers:

| exon | 5'-primer | 3'-primer |
|---|---|---|
| 1 | Seq ID No:13 | Seq ID No:14 |
| 8 | Seq ID No:15 | Seq ID No:16 |
| 18 | Seq ID No:17 | Seq ID No:18 |
| 21 | Seq ID No:19 | Seq ID No:20 |
| 22 | Seq ID No:21 | Seq ID No:22 |
| 23 | Seq ID No:23 | Seq ID No:24. |

13. A kit for identification of mutations in the retinoblastoma gene, comprising a plurality of primer pairs for multiplex coamplification of a selected plurality of exons of the retinoblastoma gene, wherein one member of each primer pair is labeled with a detectable label, and wherein the primer pairs are selected to have a common melting temperature and to produce amplification products having differing lengths and wherein the primers pairs bind to intron regions immediately flanking each of the selected plurality of exons, said kit comprising primers selected to permit coamplification of exons 6, 7, 8, 9, 10, 11, 12, and 27 of the retinoblastoma gene.

14. A kit according to claim 13, comprising the following coamplification primers:

| exon | 5'-primer | 3'-primer |
|---|---|---|
| 6 | Seq ID No:25 | Seq ID No:26 |
| 7 | Seq ID No:27 | Seq ID No:28 |
| 9 | Seq ID No:29 | Seq ID No:30 |
| 10 | Seq ID No:31 | Seq ID No:32 |
| 11 | Seq ID No:33 | Seq ID No:34 |
| 12 | Seq ID No:35 | Seq ID No:36 |
| 27 | Seq ID No:37 | Seq ID No:38. |

15. A kit for identification of mutations in the retinoblastoma gene, comprising a plurality of primer pairs for multiplex coamplification of a selected plurality of exons of the retinoblastoma gene, wherein one member of each primer pair is labeled with a detectable label, and wherein the primer pairs are selected to have a common melting temperature and to produce amplification products having differing lengths and wherein the primers pairs bind to intron regions immediately flanking each of the selected plurality of exons, said kit comprising primers selected to permit coamplification of exons 4, 14, 20, 24 and 26 of the retinoblastoma gene.

16. A kit according to claim 15, comprising the following coamplification primers:

| exon | 5'-primer | 3'-primer |
|---|---|---|
| 4 | Seq ID No:39 | Seq ID No:40 |
| 14 | Seq ID No:41 | Seq ID No:42 |
| 20 | Seq ID No:43 | Seq ID No:44 |
| 24 | Seq ID No:45 | Seq ID No:46 |
| 26 | Seq ID No:47 | Seq ID No:48. |

17. A kit for identification of mutations in the retinoblastoma gene, comprising a plurality of primer pairs for multiplex coamplification of a selected plurality of exons of the retinoblastoma gene, wherein one member of each primer pair is labeled with a detectable label, and wherein the primer pairs are selected to have a common melting temperature and to produce amplification products having differing lengths and wherein the primers pairs bind to intron regions immediately flanking each of the selected plurality of exons, said kit comprising primers selected to permit coamplification of exons 15, 16, 17, and 19 of the retinoblastoma gene.

18. A kit according to claim 17, comprising the following coamplification primers:

| exon | 5'-primer | 3'-primer |
|---|---|---|
| 15/16 | Seq ID No:49 | Seq ID No:50 |
| 17 | Seq ID No:51 | Seq ID No:52 |
| 29 | Seq ID No:53 | Seq ID No:54. |

19. A kit for identification of mutations in the retinoblastoma gene, comprising a plurality of primer pairs for multiplex coamplification of a selected plurality of exons of the retinoblastoma gene, wherein one member of each primer pair is labeled with a delectable label, and wherein the primer pairs are selected to have a common melting temperature and to produce amplification products having differing lengths and wherein the primers pairs bind to intron regions immediately flanking each of the selected plurality of exons, said kit comprising primers selected to permit coamplification of exons 4, 5, 7, 8, 10, 11, 19 and 25 in a single reaction mixture.

20. A kit for identification of mutations in the retinoblastoma gene, comprising a plurality of primer pairs for multiplex coamplification of a selected plurality of exons of the retinoblastoma gene, wherein one member of each primer pair is labeled with a detectable label, and wherein the primer pairs are selected to have a common melting temperature and to produce amplification products having differing lengths and wherein the primers pairs bind to intron regions immediately flanking each of the selected plurality of exons, said kit comprising primers selected to permit coamplification of exons 12, 15, 16, 17, 18 and 21 in a single reaction mixture.

21. A kit for identification of mutations in the retinoblastoma gene, comprising a plurality of primer pairs for multiplex coamplification of a selected plurality of exons of the retinoblastoma gene, wherein one member of each primer pair is labeled with a detectable label and wherein the primer pairs are selected to have a common melting temperature and to produce amplification products having differing lengths and wherein the primers pairs bind to intron regions immediately flanking each of the selected plurality of exons, said kit comprising primers selected to permit coamplification of exons 3, 9, 13, 20, 23 and 24 in a single reaction mixture.

22. A kit for identification of mutations in the retinoblastoma gene, comprising a plurality of primer pairs for multiplex coamplification of a selected plurality of exons of the retinoblastoma gene, wherein one member of each primer pair is labeled with a detectable label, and wherein the primer pairs are selected to have a common melting temperature and to produce amplification products having differing lengths and wherein the primers pairs bind to intron regions immediately flanking each of the selected plurality of exons, said kit comprising primers selected to permit coamlplification of exons 2, 6, 14, 22, 26 and 27 in a single reaction mixture.

23. A kit for identification of mutations in the retinoblastoma gene, comprising a plurality of primer pairs for multiplex coamplification of a selected plurality of exons of the retinoblastoma gene, wherein one member of each primer pair is labeled with a detectable label, and wherein the primer pairs are selected to have a common melting temperature and to produce amplification products having differing lengths and wherein the primers pairs bind to intron regions immediately flanking each of the selected plurality of exons, said kit further comprising a pair of sequencing primers effective to sequence at least one selected exon of the retinoblastoma gene, wherein the sequencing primers are selected from among the primers set forth in Table 2.

24. A method for identifying mutations in a sample retinoblastoma gene comprising the steps of:
   (a) quantitatively coamplifying a plurality of exons of the sample retinoblastoma gene using primers complementary to intron regions immediately flanking each of the plurality of exons to produce amplification products;
   (b) determining the lengths of the amplification products for each amplified sample exon and comparing that length to the length of amplification products obtained when a wild-type retinoblastoma gene is amplified using the same primers, whereby differences in length between an amplified sample exon and the corresponding amplified wild-type exon reflect the occurrence on an insertion or deletion mutation in the sample retinoblastoma gene; and
   (c) determining the nucleic acid sequence of each exon identified in step (b) to contain an insertion or deletion mutation, or in the event no insertion or deletion mutations are identified, determining the nucleic acid sequence of at least one exon of the retinoblastoma gene, sufficient exons being sequenced to identify the presence of a mutation if one exists in the sample retinoblastoma gene, wherein in step (b) exons 12, 15, 16, 17, 18 and 21 are coamplified in a single reaction.

25. A method for identifying mutations in a sample retinoblastoma gene comprising the steps of:
   (a) quantitatively coamplifying a plurality of exons of the sample retinoblastoma gene using primers complementary to intron regions immediately flanking each of the plurality of exons to produce amplification products;

(b) determining the lengths of the amplification products for each amplified sample exon and comparing that length to the length of amplification products obtained when a wild-type retinoblastoma gene is amplified using the same primers, whereby differences in length between an amplified sample exon and the corresponding amplified wild-type exon reflect the occurrence on an insertion or deletion mutation in the sample retinoblastoma gene; and (c) determining the nucleic acid sequence of each exon identified in step (b) to contain an insertion or deletion mutation, or in the event no insertion or deletion mutations are identified, determining the nucleic acid sequence of at least one exon of the retinoblastoma gene, sufficient exons being sequenced to identify the presence of a mutation if one exists in the sample retinoblastoma gene, wherein in step (a) exons 3, 9, 13, 20, 23 and 24 are coamplified in a single reaction.

26. A method for identifying mutations in a sample retinoblastotna gene comprising the steps of:

(a) quantitatively coamplifying a plurality of exons of the sample retinoblastoma gene using primers complementary to intron regions immediately flanking each of the plurality of exons to produce amplification products;

(b) determining the lengths of the amplification products for each amplified sample exon and comparing that length to the length of amplification products obtained when a wild-type retinoblastoma gene is amplified using the same primers, whereby differences in length between an amplified sample exon and the corresponding amplified wild-type exon reflect the occurrence on an insertion or deletion mutation in the sample retinoblastoma gene; and (c) determining the nucleic acid sequence of each exon identified in step (b) to contain an insertion or deletion mutation, or in the event no insertion or deletion mutations are identified, determining the nucleic acid sequence of at least one exon of the retinoblastoma gene, sufficient exons being sequenced to identify the presence of a mutation if one exists in the sample retinoblastoma gene, wherein in step (a) exons 2, 6, 14, 22, 26 and 27 are coamplified in a single reaction.

27. A reagent mixture comprising any of the primer pairs set forth in Table 1.

* * * * *

UNITED STATES PATENT AND TRADEMARK OFFICE
CERTIFICATE OF CORRECTION

| | | |
|---|---|---|
| PATENT NO. | : 6,063,567 | Page 1 of 1 |
| APPLICATION NO. | : 08/779916 | |
| DATED | : May 16, 2000 | |
| INVENTOR(S) | : Gallie et al. | |

It is certified that error appears in the above-identified patent and that said Letters Patent is hereby corrected as shown below:

On the Title page,

Item [74], "Oppendahl" should read -- Oppedahl --

Signed and Sealed this

Eighteenth Day of May, 2010

David J. Kappos
*Director of the United States Patent and Trademark Office*